(12) United States Patent
Min et al.

(10) Patent No.: US 12,390,148 B2
(45) Date of Patent: *Aug. 19, 2025

(54) SPINAL CORD STIMULATION GUIDANCE SYSTEM AND METHOD OF USE

(71) Applicant: Pacesetter, Inc., Sylmar, CA (US)

(72) Inventors: Xiaoyi Min, Camarillo, CA (US); Alexander Kent, Mountain View, CA (US)

(73) Assignee: Pacesetter, Inc., Sylmar, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/457,629

(22) Filed: Aug. 29, 2023

(65) Prior Publication Data

US 2023/0397875 A1     Dec. 14, 2023

Related U.S. Application Data

(60) Continuation of application No. 16/248,144, filed on Jan. 15, 2019, now Pat. No. 11,786,166, which is a
(Continued)

(51) Int. Cl.
*A61B 5/00*     (2006.01)
*A61B 5/0536*   (2021.01)
(Continued)

(52) U.S. Cl.
CPC ............ *A61B 5/407* (2013.01); *A61B 5/0536* (2013.01); *A61B 5/0537* (2013.01); *A61B 5/388* (2021.01); *A61B 5/4887* (2013.01); *A61B 5/6823* (2013.01); *A61N 1/37247* (2013.01); *A61N 1/3787* (2013.01); *G16H 20/40* (2018.01);
(Continued)

(58) Field of Classification Search
None
See application file for complete search history.

(56) References Cited

U.S. PATENT DOCUMENTS 7,146,224 B2   12/2006   King
7,174,215 B2   2/2007    Bradley
(Continued)

*Primary Examiner* — Jacqueline Cheng
*Assistant Examiner* — Samuel C Kim
(74) *Attorney, Agent, or Firm* — Dean D. Small; The Small Patent Law Group, LLC

(57) ABSTRACT

A system and method for modeling patient-specific spinal cord stimulation (SCS) is disclosed. The system and method acquire impedance and evoked compound action potential (ECAP) signals from a lead positioned proximate to a spinal cord (SC). The lead includes at least one electrode. The system and method determine a patient-specific anatomical model based on the impedance and ECAP signals, and transform a dorsal column (DC) map template based on a DC boundary of the patient-specific anatomical model. Further, the system and method map the transformed DC map template to the patient-specific anatomical model. The system and method may also include the algorithms to solve extracellular and intracellular domain electrical fields and propagation along neurons. The system and method may also include the user interfaces to collect patient responses and compare with the patient-specific anatomical model as well as using the patient-specific anatomical model for guiding SCS programming.

14 Claims, 24 Drawing Sheets

| IMPEDANCE | ECAP AMPLITUDE | DETERMINATION | |
|---|---|---|---|
| INCREASE | DECREASE | LEAD MOVEMENT AWAY FROM SPINAL CORD TISSUE | 2810 |
| NO CHANGE | DECREASE | LEAD MOVEMENT AWAY FROM SPINAL CORD TISSUE | 2812 |
| DECREASE | INCREASE | LEAD MOVEMENT TOWARD FROM SPINAL CORD TISSUE | 2814 |
| NO CHANGE | INCREASE | LEAD MOVEMENT TOWARD SPINAL CORD TISSUE | 2816 |
| NO CHANGE | DECREASE GREATER THAN CRITICAL THRESHOLD | TISSUE DAMAGE BY OVER STIMULATION | 2820 |
| NO CHANGE | INCREASE, AFTER A TIME PERIOD DECREASE GREATER THAN CRITICAL THRESHOLD | TISSUE DAMAGE BY PRESSURE FROM LEAD | 2821 |
| INCREASE/DECREASE | NO CHANGE | SUBSTRATE CHANGE | 2808 |

Related U.S. Application Data division of application No. 14/958,725, filed on Dec. 3, 2015, now Pat. No. 10,213,148.

(60) Provisional application No. 62/088,451, filed on Dec. 5, 2014.

(51) Int. Cl.

| | | |
|---|---|---|
| *A61B 5/0537* | (2021.01) | |
| *A61B 5/388* | (2021.01) | |
| *A61N 1/372* | (2006.01) | |
| *A61N 1/378* | (2006.01) | |
| *G16H 20/40* | (2018.01) | |
| *G16H 40/63* | (2018.01) | |
| *A61N 1/05* | (2006.01) | |
| *G16H 20/30* | (2018.01) | |
| *G16H 30/40* | (2018.01) | |

(52) U.S. Cl.
CPC ........ *G16H 40/63* (2018.01); *A61B 2562/046* (2013.01); *A61N 1/0553* (2013.01); *G16H 20/30* (2018.01); *G16H 30/40* (2018.01)

(56) References Cited

U.S. PATENT DOCUMENTS

| | | | |
|---|---|---|---|
| 7,216,001 | B2 | 5/2007 | Hacker et al. |
| 8,504,160 | B2 | 8/2013 | Lee et al. |
| 8,543,217 | B2 | 9/2013 | Stone et al. |
| 9,302,112 | B2 | 4/2016 | Bornzin et al. |
| 9,381,356 | B2 | 7/2016 | Parker et al. |
| 11,786,166 | B2 * | 10/2023 | Min .................... A61B 5/4887 600/547 |
| 2008/0009764 | A1 | 1/2008 | Davies |
| 2010/0145222 | A1 | 6/2010 | Brunnett et al. |
| 2010/0152812 | A1 | 6/2010 | Flaherty et al. |
| 2012/0083709 | A1 | 4/2012 | Parker et al. |
| 2013/0006324 | A1 | 1/2013 | Bradley |
| 2014/0148726 | A1 | 5/2014 | Wagner |
| 2014/0236257 | A1 | 8/2014 | Parker et al. |
| 2014/0277282 | A1 * | 9/2014 | Jaax .................... A61N 1/36139 607/59 |
| 2015/0005846 | A1 * | 1/2015 | Ranu .................. A61N 1/36521 607/59 |
| 2015/0174366 | A1 * | 6/2015 | Taha ................. A61M 25/0043 607/46 |
| 2015/0224326 | A1 | 8/2015 | Toth et al. |
| 2016/0121124 | A1 * | 5/2016 | Johanek .............. A61N 1/37247 607/62 |
| 2016/0166164 | A1 | 6/2016 | Obradivuc et al. |

* cited by examiner

| IMPEDANCE | ECAP AMPLITUDE | DETERMINATION |
|---|---|---|
| INCREASE | DECREASE | LEAD MOVEMENT AWAY FROM SPINAL CORD TISSUE |
| NO CHANGE | DECREASE | LEAD MOVEMENT AWAY FROM SPINAL CORD TISSUE |
| DECREASE | INCREASE | LEAD MOVEMENT TOWARD FROM SPINAL CORD TISSUE |
| NO CHANGE | INCREASE | LEAD MOVEMENT TOWARD SPINAL CORD TISSUE |
| NO CHANGE | DECREASE GREATER THAN CRITICAL THRESHOLD | TISSUE DAMAGE BY OVER STIMULATION |
| NO CHANGE | INCREASE, AFTER A TIME PERIOD DECREASE GREATER THAN CRITICAL THRESHOLD | TISSUE DAMAGE BY PRESSURE FROM LEAD |
| INCREASE/DECREASE | NO CHANGE | SUBSTRATE CHANGE |

FIG. 28

SPINAL CORD STIMULATION GUIDANCE SYSTEM AND METHOD OF USE

RELATED APPLICATION DATA

This application is a continuation of U.S. application Ser. No. 16/248,144, filed 15 Jan. 2019, which is a divisional of U.S. application Ser. No. 14/958,725, filed 3 Dec. 2015 (now U.S. Pat. No. 10,213,148, issued 26 Feb. 2019), which claims priority from U.S. Application No. 62/088,451 filed 5 Dec. 2014, each entitled "SPINAL CORD STIMULATION GUIDANCE SYSTEM AND METHOD OF USE," all of which are hereby expressly incorporated by reference in their entirety.

BACKGROUND OF THE INVENTION

Embodiments of the present disclosure generally relate to neurostimulation (NS) systems, and more particularly to model-based programming guidance for implantation of spinal cord stimulation (SCS) systems.

NS systems are devices that generate electrical pulses and deliver the pulses to nervous tissue to treat a variety of disorders. For example, SCS has been used to treat chronic and intractable pain. Another example is deep brain stimulation, which has been used to treat movement disorders such as Parkinson's disease and affective disorders such as depression. While a precise understanding of the interaction between the applied electrical energy and the nervous tissue is not fully appreciated, it is known that application of electrical pulses depolarizes neurons and generate propagating action potentials into certain regions or areas of nerve tissue. The propagating action potentials effectively mask certain types of pain transmitted from regions, increase the production of neurotransmitters, or the like. For example, applying electrical energy to the spinal cord associated with regions of the body afflicted with chronic pain can induce "paresthesia" (a subjective sensation of numbness or tingling) in the afflicted bodily regions. Inducing this artificial sensation replaces the feeling of pain in the body areas effectively masking the transmission of non-acute pain sensations to the brain.

Computational modeling of SCS, through coupled three dimensional (3-D) electrical field and nerve fiber kinetic models, can provide a tool for assessing the effectiveness of the SCS and/or a placement of the NS system within the patient. However, current modeling approaches commonly require commercial software packages that involve computationally-intensive steps, such as: obtain magnetic resonance imaging (MRI) of the patient; perform tissue segmentation on the medical images to create a 3-D spinal cord (SC) geometrical model; position the implanted leads within the SC model; specify stimulation contacts on the lead and set boundaries to contact-voltage/current condition; mesh the models; and in two stages solve for the electrical fields and activation regions in the dorsal column (DC) and dorsal root (DR) of the SC; and determine stimulation thresholds and activated dermatomal fiber zones. The process requires multiple software packages and specialized personnel to perform the tasks, which make conventional modeling approach difficult in the clinical setting.

However, some of the SCS systems available are not MRI-compatible, requiring MRI images to be taken prior to implant of the SCS system, and other modalities (e.g., X-rays, computed tomography (CT) scan) are needed to determine SCS lead position after implant. Moreover, detailed SC anatomy is difficult to ascertain with clinical MRI sequences, with dermatomal fiber tracts from such MRI images being difficult to visualize. Further, solving the computational model with the conventional approach is time-consuming, making this difficult to use in the clinical setting during an office visit or SCS implant. A need exists to overcome the shortcomings of traditional modeling methods.

SUMMARY

In accordance with one embodiment, a method for modeling patient-specific spinal cord stimulation (SCS). The method may include acquiring impedance and evoked compound action potential (ECAP) signals from a lead positioned proximate to a spinal cord (SC). The lead may include at least one electrode. The method may include determining a patient-specific anatomical model based on the impedance and ECAP signals, and transforming a dorsal column (DC) map template based on a DC boundary of the patient-specific anatomical model. Optionally, the method may include acquiring additional impedance and ECAP signals. Each pair of impedance and ECAP signals may be acquired while the patient is in different patient postures or positions, such as sitting, standing, supine, or the like. Additionally, or alternatively, the method may include detecting neural tissue damage based on the impedance and ECAP signals.

Further, the method may include extruding the patient-specific anatomical model along an SC axis to create a three-dimensional model within a structural grid with material index assigned to each element. The geometry and location of the distal SCS leads are mapped into the 3D grids with their material properties assigned. The method may include solving a fully coupled extracellular and intracellular domain (e.g., a Bidomain Model) for electromagnetic fields in the extracellular domain and electrical propagation along neurons in the intracellular domain including dorsal column (DC), dorsal root (DR), or dorsal root ganglion (DRG).

Additionally, the method may include receiving patient responses at one or more pre-selected stimulation configurations and/or patient positions. The patient response may correspond to coverage zones on a body map as indicated on user interface at specific stimulation pulses for each of the pre-selected stimulation configurations.

Furthermore, the method may include using predetermined or user defined stimulation configurations for emitting a stimulation pulse from the at least one electrode, measuring a stimulation return signal in response to the stimulation pulse, and iteratively repeating the emitting and measuring operation of the method for each electrode to form a solution matrix corresponding to the coupled extracellular and intracellular domains.

In an embodiment, a system for modeling patient-specific spinal cord stimulation (SCS). The system may include a lead positioned proximate to a spinal cord (SC). The lead may include at least one electrode configured to acquire impedance and evoked compound action potential (ECAP) signals. The system may also include a system in communication with the lead. The system may include a memory device, a processor and a display. The system may be configured to determine a patient-specific anatomical model based on the impedance and ECAP signals, transform a dorsal column (DC) map template based on a DC boundary of the patient-specific anatomical model, and map the transformed DC map template to the patient-specific anatomical model. The system may also include algorithms to solve extracellular and intracellular domain electrical fields and propagation along neurons. The system may also include the user interfaces to collect patient responses and compare with model solutions.

In an embodiment, a method for differentiating spinal cord (SC) damage. The method may include emitting a stimulation waveform from at least one electrode of a lead. The lead being positioned proximate to a SC. The method may include acquiring impedance and evoked action compound action potential (ECAP) signals. The impedance and ECAP signals are based on the stimulation waveform. The method may further include selecting a first impedance and ECAP measurement and a second impedance and ECAP measurement from the impedance and ECAP signals. The second impedance and ECAP measurement is temporally separated from the first impedance and ECAP measurement. The method may include detecting SC tissue damage based on a difference between the second ECAP measurement and the first ECAP measurement, and between the second impedance measurement and first impedance measurement, and adjusting at least one therapy parameter to change the stimulation waveform or adjusting the position of the lead based on detection of the SC tissue damage.

BRIEF DESCRIPTION OF THE DRAWINGS

FIG. 28 is a decision table for detecting spinal cord tissue damage, substrate change, and/or movement of a lead, in accordance to an embodiment of the present disclosure.

DETAILED DESCRIPTION

While multiple embodiments are described, still other embodiments of the described subject matter will become apparent to those skilled in the art from the following detailed description and drawings, which show and describe illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

Embodiments described herein include a patient-specific spinal cord stimulation (SCS) programming guidance system 100 that may be used during SCS implantation, during office visits, and the like. The system 100 may be used by a clinician and/or patient to determine and/or select optimal SCS settings (e.g., amplitude, duration, frequency, type of stimulation pulses, selection of electrode configurations, or the like) that target a region of interest.

Figure 1:
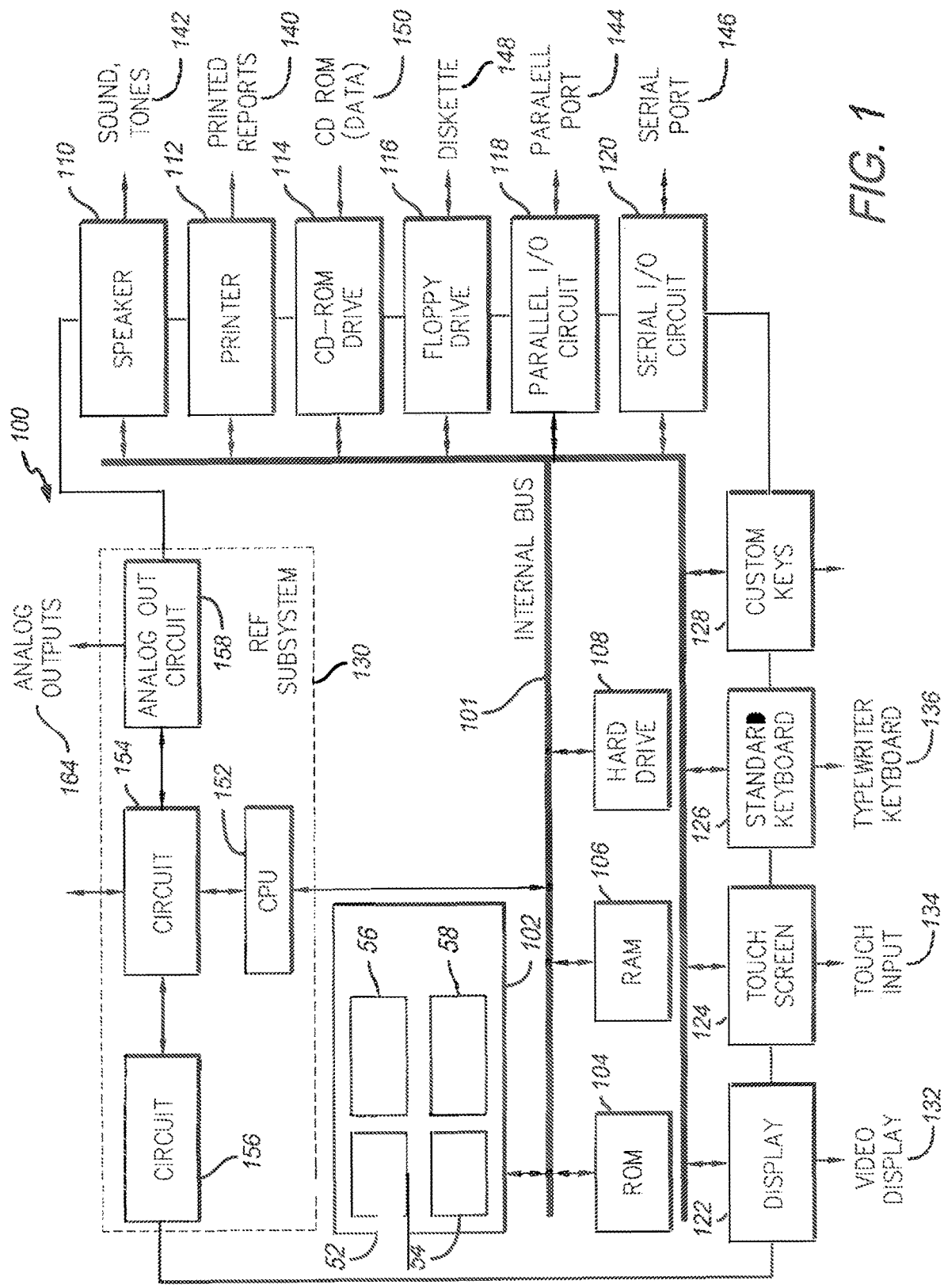
FIG. 1 is a functional block diagram of a spinal cord stimulation programming guidance system, in accordance to an embodiment of the present disclosure.

FIG. 1 illustrates a functional block diagram of the SCS programming guidance system 100, that is operated in accordance with the processes described herein and to interface with an NS system 200 (FIG. 2) as described herein. The system 100 may be a workstation, a portable computer, a tablet computer, a PDA, a cell phone and the like. The system 100 includes an internal bus 101 that may connect/interface with a Central Processing Unit ("CPU") 102, ROM 104, RAM 106, a hard drive 108, a speaker 110, a printer 112, a CD-ROM drive 114, a floppy drive 116, a parallel I/O circuit 118, a serial I/O circuit 120, the display 122, a touchscreen 124, a standard keyboard 126, custom keys 128, and an RF subsystem 130. The internal bus 101 is an address/data bus that transfers information between the various components described herein. The hard drive 108 may store operational programs as well as data, such as stimulation waveform templates and detection thresholds.

Optionally, the touchscreen 124 may be integrated with the display 122. The keyboard 126 (e.g., a typewriter keyboard 136) allows the user to enter data to the displayed fields, as well as interface with the RF subsystem 130. Furthermore, custom keys 128, for example, may turn on/off the system 100. The printer 112 prints copies of reports 140 for a physician to review or to be placed in a patient file, and the speaker 110 provides an audible warning (e.g., sounds and tones 142) to the user. The parallel I/O circuit 118 interfaces with a parallel port 144. The serial I/O circuit 120 interfaces with a serial port 146. The floppy drive 116 accepts diskettes 148. Optionally, the serial I/O port may be coupled to a USB port or other interface capable of communicating with a USB device such as a memory stick. The CD-ROM drive 114 accepts CD-ROMs 150.

The CPU 102 typically includes a microprocessor, a micro-controller, or equivalent control circuitry, designed specifically to control interfacing with the system 100 and with the NS system 200. The CPU 102 may include RAM or ROM memory, logic and timing circuitry, state machine circuitry, and I/O circuitry to interface with the NS system 200. The display 122 (e.g., may be connected to the video display 132). The display 122 displays various information related to the processes described herein. The touchscreen 124 may display graphic information relating to the NS system 200 (e.g., stimulation levels, stimulation waveforms, ECAP measurements) and include a graphical user interface.

The system 100 includes components 52-58 that may employ structures or aspects of various embodiments (e.g., systems and/or methods) discussed herein. In various embodiments, certain components (or operations) may be added, certain components may be combined, certain components may be performed simultaneously, certain components may be performed concurrently, certain components may be split into multiple components, certain components may be performed in a different order, or certain components may be re-performed in an iterative fashion. The components 52-58 may be a part of the CPU 102. Additionally, or alternatively, the components 52-58 may be algorithms or instructions performed by the CPU 102 stored in memory (e.g., ROM 104, RAM 106, hard drive 108). Optionally, the components 52-58 may be separate modules in communication with the CPU 102. Optionally, one or more of the components 52-58 may be located external to the system 102. The system 102 may receive data from the components 52-58 via the RF subsystem 130.

Generally, the component 52 may be configured to generate lead position geometrical models, which illustrate a position of one or more electrodes on a lead with respect to a spinal cord (SC) tissue of interest based on measured impedance and evoked compound action potential (ECAP) signals. For example, the impedance signal is received by one or more electrodes, which is used to determine a distance between a select electrode and the SC tissue of interest. The geometrical models may additionally define anatomical parameters of interest (e.g., a thickness of cerebral spinal fluid) and landmark locations (e.g., position of the electrodes with respect to the SC tissue of interest) of the SC at select vertebral levels of interest based on the impedance and ECAP signals. For example, based on a structure of the ECAP signal (e.g., slope, peak to peak amplitude, peak latency, peak duration) received by one or more electrodes may be used to determine thickness of the cerebral spinal fluid. The component 52 may also be configured to use lookup tables (e.g., databases) of impedance and ECAP information from computational simulations, which are compared with the measured impedance and ECAP signals to determine a distance from the electrodes to dura/cerebral spinal fluid (CSF) and CSF thickness. Based on the measured impedance and ECAP signals, the component 52 may adjust a SC model template to match the patient's anatomy to generate the lead position geometric models.

The component 54 may be configured to transform (e.g., morph) a dermatomal map template of the SC dorsal column (DC) to fit a derived patient specific DC model based on an anatomy of a patient. Optionally, the transforming of the dermatomal map template by the component 54 may include meshing the dermatomal zone map template and deforming the mesh to adjust to the outer boundary shape of the patient's DC anatomy, such as, using Delaunay triangulation. The outer boundary shape of the patient's DC anatomy may be determined based on the anatomical parameters of interest and landmark locations determined from the lead position geometric model. Additionally, or alternatively, the component 54 may include shifting pixels of the dermatomal zone map template according to a distance the nodes moved from the original mesh to the deformed mesh during the transformation operation. Optionally, variations may be added to the transforming or pixel movement to account for uncertainties in the dermatomal zone size and boundary locations.

Based on the lead position geometric model generated from the component 52 and the derived patient specific DC model from the component 54, the component 56 may be configured to generate a two-dimensional (2D) and/or three-dimensional (3D) SC model. The SC model may be used to compute electrical fields and neural transmembrane potential in the DC, dorsal root (DR), or dorsal root ganglion (DRG). Further the SC model may be used to determine the activation regions and activation of mapped dermatomal zones for corresponding electrodes. The SC model may include a fully coupled extracellular and intracellular domain for electromagnetic fields in the extracellular domain and electrical propagation along neurons in the intracellular domain. A technical effect of the system 100 eliminates the use of commercial simulation software using conventional finite element analysis (FEA) and finite difference (FD) methods. An additional technical effect of the system 100 may be to perform a discretization from a 2D SC model to a 3D SC model with the SCS lead that is much faster than other meshing methods used in FEA.

The component 58 may be configured to apply pre-selected or selected electrode stimulation configurations received from the clinician and/or patient. Additionally, or alternatively, the component 58 may be configured to test and refine the SC model based on feedback by the patient.

Optionally, the component 58 may include a user-interface, which may include a graphical user interface, for entering stimulation parameters with a display of the corresponding activation regions and activated dermatomal zones.

The RF subsystem 130 includes a central processing unit (CPU) 152 in electrical communication with RF circuitry 154, which may communicate with both memory 156 and an analog out circuit 158. The analog out circuit 158 includes communication circuits to communicate with analog outputs 164. The system 100 may wirelessly communicate with the NS system 200 using a telemetry system. Additionally, or alternatively, the system 100 may wirelessly communicate with the NS system 200 utilize wireless protocols, such as Bluetooth, Bluetooth low energy, Wi-Fi, MICS, and the like. Alternatively, a hard-wired connection may be used to connect the system 100 to the NS system 200.

Figure 2:
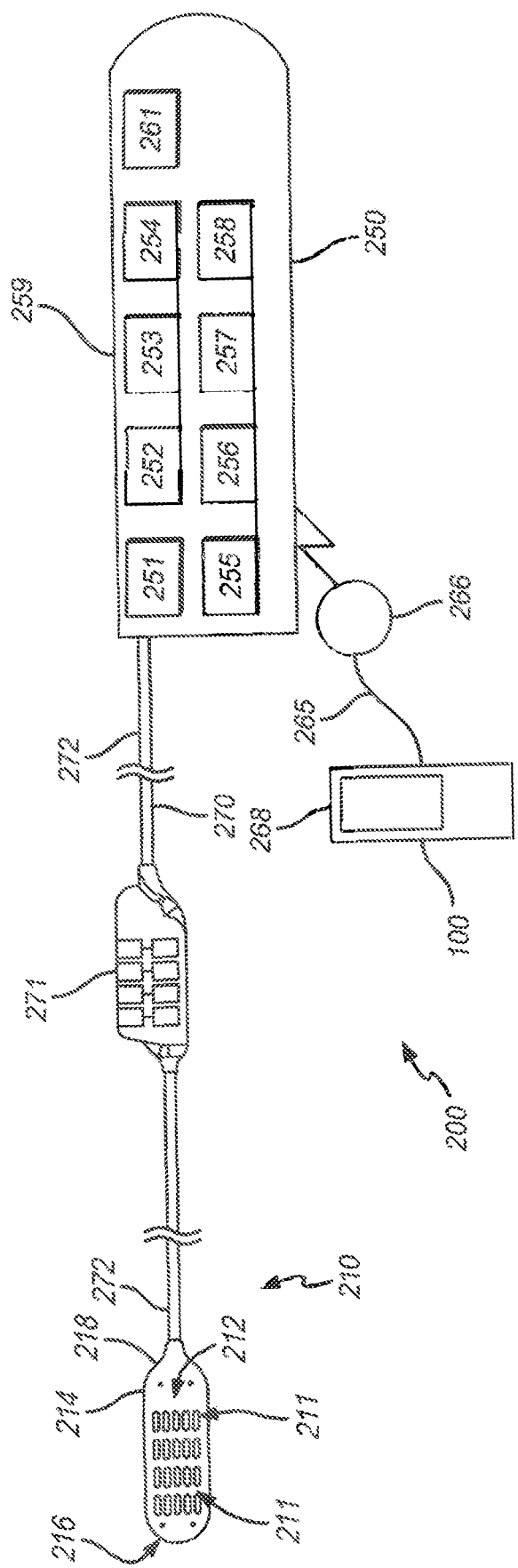
FIG. 2 illustrates a neurostimulation system that is a part of or used by one or more of the components of FIG. 1.

Optionally, the system 100 may transmit the stimulation database request to an implantable pulse generator (IPG) 250 (FIG. 2). For example, the user may instruct the system 100 to transmit a stimulation database request from the graphical user interface on the touchscreen 124, the keyboard 126, or the like. An NS system 200 receives the request via communication circuitry 255 and transmits the stimulation database stored in memory 261 to the system 100.

FIG. 2 depicts the NS system 200 that may be a part of or used by one or more of the components 52-58. The NS system 200 generates electrical pulses for application to tissue of a patient and/or measures/senses electrical signals in response to the electrical pulses according to one embodiment. For example, the NS system 200 may be adapted to stimulate spinal cord tissue, dorsal root, dorsal root ganglion, peripheral nerve tissue, deep brain tissue, cortical tissue, cardiac tissue, digestive tissue, pelvic floor tissue, or any other suitable nerve tissue of interest within a patient's body.

The NS system 200 includes the IPG 250 that is adapted to generate electrical pulses for application to tissue of a patient. The IPG 250 typically comprises a metallic housing or can 259 that encloses a controller 251, pulse generating circuitry 252, a charging coil 253, a battery 254, a far-field and/or near field communication circuitry 255, battery charging circuitry 256, switching circuitry 257, sensing circuitry 258, memory 261, and the like. The controller 251 typically includes a microcontroller or other suitable processor for controlling the various other components of the device. Software code may be stored in memory 261 of the IPG 250 or integrated with the controller 251 for execution by the microcontroller or processor to control the various components of the device.

The IPG 250 may comprise a separate or an attached extension component 270. If the extension component 270 is a separate component, the extension component 270 may connect with a "header" portion of the IPG 250 as is known in the art. If the extension component 270 is integrated with the IPG 250, internal electrical connections may be made through respective conductive components. Within the IPG 250, electrical pulses are generated by the pulse generating circuitry 252 and are provided to the switching circuitry 257. The switching circuitry 257 connects to outputs of the IPG 250. Electrical connectors (e.g., "Bal-Seal" connectors) within the connector portion 271 of the extension component 270 or within the IPG header may be employed to conduct various stimulation pulses. The terminals of one or more leads 210 are inserted within the connector portion 271 or within the IPG header for electrical connection with respective connectors. Thereby, the pulses originating from the IPG 250 are provided to the one or more leads 210. The pulses are then conducted through the conductors of the lead 210 and applied to tissue of a patient via one or more electrodes (e.g., array of electrodes 211). Any suitable known or later developed design may be employed for connector portion 272.

The lead 210 is connected to a flat, thin, paddle structure 214 and connect thereto in a general longitudinal alignment with the length of the paddle structure 214. The paddle structure 214 may be formed from a medical grade, substantially inert material, for example, polyurethane, silicone, or the like. A front surface or face 212 of the paddle structure 214 is depicted in FIG. 2, which includes an array of electrodes 211 that are spaced apart longitudinally along the length of the paddle structure 214 from a distal end 216 and a proximal end 218. The array of electrodes 211 are spaced apart across the width of the paddle structure 214. The spacing of the electrodes 211 can be set accordingly to a target site (e.g., proximate to the SC) and the needed stimulation. The paddle structure 214 itself may have a width such that it spans the entire dorsal column or fits within the epidural space. For example, depending upon the desired implantation site, thoracic or cervical, the paddle structure 214 may be designed to fit into the desired space such that it at least covers the anatomical and physiological midline of the patient. Additionally, or alternatively, the paddle structure 214 may be similar to the paddle structure disclosed in U.S. Provisional Application No. 61/791,288, entitled, "PADDLE LEADS FOR NEUROSTIMULATION AND METHOD OF DELIVERYING THE SAME," which is expressly incorporated herein by reference.

Each of the electrodes 211 are mutually separated by non-conducting or insulative material of the paddle, which electrically isolate each electrode 211 from adjacent electrodes 211. The non-conducting material may include one or more insulative materials and/or biocompatible materials to allow the paddle structure 214 and lead 210 to be implantable within the patient. Non-limiting examples of such materials include polyimide, polyetheretherketone (PEEK), polyethylene terephthalate (PET) film (also known as polyester or Mylar), polytetrafluoroethylene (PTFE) (e.g., Teflon), or parylene coating, polyether bloc amides, polyurethane.

The electrodes 211 may be formed of non-corrosive, highly conductive material. For example, stainless steel, MP35N, platinum, platinum alloys, or the like. The electrodes 211 may be set to function as cathodes, anodes or set to a high-impedance state for a given pulse according to the pulses generated from the IPG 250. The electrodes 211 may be configured to emit the pulses in an outward radial direction proximate to or within a stimulation target. The electrodes 211 may also be configured to acquire electrical potential measurements (e.g., voltage, current) or electrical signals for the sensory circuit 258, such as evoked compound activation potentials (ECAP) emitted from the stimulation target. ECAP signals may be generated by neuronal transmembrane currents of neurons activated following or in response to a stimulation pulse from one or more of the electrodes 211.

Optionally, the IPG 250 may have more than one lead 210 connected via the connector portion 271 of the extension component 270 or within the IPG header. Additionally, or alternatively, the electrodes 211 of each lead 210 may be configured separately to emit current pulses or measure electrical signals emitted from and/or proximate the stimulation target.

It should be noted that in other embodiments the electrodes 211 may be in various other formations or structures. For example, the electrodes 211 may be in the shape of a ring such that each electrode 211 continuously covers the circumference of the exterior surface of the lead 210 to form a percutaneous lead structure. Each of the ring electrodes 211 are separated by non-conducting rings, which electrically isolate each electrode 211 from an adjacent electrode 211. In another example, the electrodes 211 may be in the shape of a split or non-continuous ring such that the pulse may be directed in an outward radial direction adjacent to the electrodes 211. Further examples of a fabrication process of the electrodes 211 is disclosed in U.S. patent application Ser. No. 12/895,096, entitled, "METHOD OF FABRICATING STIMULATION LEAD FOR APPLYING ELECTRICAL STIMULATION TO TISSUE OF A PATIENT," which is expressly incorporated herein by reference.

The lead 210 may comprise a lead body 272 of insulative material about a plurality of conductors within the material that extend from a proximal end of lead 210 (proximate to the IPG 250) to its distal end (proximate to the paddle structure 214). The conductors electrically couple a plurality of the electrodes 211 to a plurality of terminals (not shown) of the lead 210. The terminals are adapted to receive electrical pulses and the electrodes 211 are adapted to apply the pulses to the stimulation target of the patient. Also, sensing of physiological signals may occur through the electrodes 211, the conductors, and the terminals. It should be noted that although the paddle structure 214 of the lead 210 is depicted with a five by four array of electrodes 211, in other embodiments, the lead 210 may be connected to any suitable number of electrodes 211 (e.g., an array with more electrodes 211 than shown in FIG. 2, an array with less electrodes 211 than shown in FIG. 2) as well as terminals, and internal conductors. Additionally, or alternatively, various sensors (e.g., a position detector, a radiopaque fiducial) may be located at or near the distal end 216 of the paddle structure 214 and electrically coupled to terminals through conductors within the lead body 272.

Although not required for all embodiments, the lead body 272 of the lead 210 may be fabricated to flex and elongate upon implantation or advancing within the tissue (e.g., nervous tissue) of the patient towards the stimulation target and movements of the patient during or after implantation. By fabricating the lead body 272, according to some embodiments, the lead body 272 or a portion thereof is capable of elastic elongation under relatively low stretching forces. Also, after removal of the stretching force, the lead body 272 may be capable of resuming its original length and profile. For example, the lead body may stretch 10%, 20%, 25%, 35%, or even 50% at forces of about 0.5, 1.0, and/or 2.0 pounds of stretching force. Fabrication techniques and material characteristics for "body compliant" leads are disclosed in greater detail in U.S. Provisional Patent Application No. 60/788,518, entitled "Lead Body Manufacturing," which is expressly incorporated herein by reference.

For implementation of the components within the IPG 250, a processor and associated charge control circuitry for an IPG is described in U.S. Pat. No. 7,571,007, entitled "SYSTEMS AND METHODS FOR USE IN PULSE GENERATION," which is expressly incorporated herein by reference. Circuitry for recharging a rechargeable battery (e.g., battery charging circuitry 256) of an IPG (e.g., the IPG 250) using inductive coupling and external charging circuits are described in U.S. Pat. No. 7,212,110, entitled "IMPLANTABLE DEVICE AND SYSTEM FOR WIRELESS COMMUNICATION," which is expressly incorporated herein by reference.

An example and discussion of "constant current" pulse generating circuitry (e.g., pulse generating circuitry 252) is provided in U.S. Patent Publication No. 2006/0170486 entitled "PULSE GENERATOR HAVING AN EFFICIENT FRACTIONAL VOLTAGE CONVERTER AND METHOD OF USE," which is expressly incorporated herein by reference. One or multiple sets of such circuitry may be provided within the IPG 250. Different pulses on different electrodes 211 may be generated using a single set of the pulse generating circuitry 252 using consecutively generated pulses according to a "multi-stimset program" as is known in the art. Complex pulse parameters may be employed such as those described in U.S. Pat. No. 7,228,179, entitled "Method and apparatus for providing complex tissue stimulation patterns," and International Patent Publication Number WO 2001/093953 A1, entitled "NEUROMODULATION THERAPY SYSTEM," which are expressly incorporated herein by reference. Alternatively, multiple sets of such circuitry may be employed to provide pulse patterns (e.g., tonic stimulation waveform, burst stimulation waveform) that include generated and delivered stimulation pulses through various electrodes of one or more leads 211 as is also known in the art. Various sets of parameters may define the pulse characteristics and pulse timing for the pulses applied to the various electrodes 211 as is known in the art. Although constant current pulse generating circuitry is contemplated for some embodiments, any other suitable type of pulse generating circuitry may be employed such as constant voltage pulse generating circuitry.

The sensing circuitry 258 may measure an electric potential (e.g., voltage, current) over time of the stimulation target or proximate tissue through at least one of the electrodes 211 that is proximate to the stimulation target. The electric potential (EP) measurements may correspond to the ECAP signal generated by the stimulation target in response to pulses emitted from the electrodes 211. For example, the sensing circuitry 258 may measure an ECAP signal from an Aβ sensory fiber or neural tissue of the SC processed from the EP sensed from one or more of the electrodes 211 on the lead 210. The sensing circuitry 258 may include amplifiers, filters, analog to digital converters, memory storage devices (e.g., RAM, ROM), digital signal processors, and/or the like. Optionally, the sensing circuitry 258 may store the EP in the memory 261.

The system 100 may be implemented to charge/recharge the battery 254 of the IPG 250 (although a separate recharging device could alternatively be employed), to access the memory 261, and to program the IPG 250 on the pulse specifications while implanted within the patient. Although, in alternative embodiments separate programmer devices may be employed for charging and/or programming the NS system 200. The system 100 may be a processor-based system that possesses wireless communication capabilities. Software may be stored within a non-transitory memory of the system 100, which may be executed by the processor to control the various operations of the system 100. Optionally, a "wand" 265 may be electrically connected to the system 100 through suitable electrical connectors (not shown). The electrical connectors may be electrically connected to a telemetry component 266 (e.g., inductor coil, RF transceiver) at the distal end of wand 265 through respective wires (not shown) allowing bi-directional communication with the IPG 250.

The user may initiate communication with the IPG 250 by placing the wand 265 proximate to the NS system 200. Preferably, the placement of the wand 265 allows the telemetry system of the wand 265 to be aligned with the far-field and/or near field communication circuitry 255 of the IPG 250. The system 100 preferably provides one or more user interfaces 268 (e.g., graphical user interface, display, touchscreen 124, keyboard 126, mouse, buttons, or the like) allowing the user to operate (e.g., adjust the pulse settings) the IPG 250. The system 100 may be controlled by the user (e.g., doctor, clinician) through the user interface 268 allowing the user to interact with the IPG 250. The user interface 268 may permit the user to move electrical stimulation along and/or across one or more of the lead(s) 210 using different electrode 211 combinations, for example, as described in U.S. Patent Application Publication No. 2009/0326608, entitled "METHOD OF ELECTRICALLY STIMULATING TISSUE OF A PATIENT BY SHIFTING A LOCUS OF STIMULATION AND SYSTEM EMPLOYING THE SAME," which is expressly incorporated herein by reference. Optionally, the user interface 268 may permit the user to designate which electrodes 211 are to stimulate (e.g., emit current pulses, in an anode state, in a cathode state) the stimulation target, to measure the ECAP or impedance (e.g., connecting to the sensing circuitry 158) resulting from the current pulses, remain inactive (e.g., floating), or the like. Additionally, or alternatively, the system 100 may access or download the electrical measurements from the memory 261 acquired by the sensing circuitry 258.

Also, the system 100 may permit operation of the IPG 250 according to one or more spinal cord stimulation (SCS) programs or therapies to treat the patient. Each SCS program may include one or more sets of stimulation parameters of the pulse including pulse amplitude, stimulation level, pulse width, pulse frequency or inter-pulse period, pulse repetition parameter (e.g., number of times for a given pulse to be repeated for respective stimset during execution of program), biphasic pulses, monophasic pulses, etc., forming a drive signal or stimulation waveform. The IPG 250 may modify its internal parameters in response to the control signals from the system 100 to vary the stimulation characteristics of the stimulation pulses transmitted through the lead 210 to the tissue of the patient. NS systems, stimsets, and multi-stimset programs are discussed in PCT Publication No. WO 01/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are expressly incorporated herein by reference.

Figure 3:
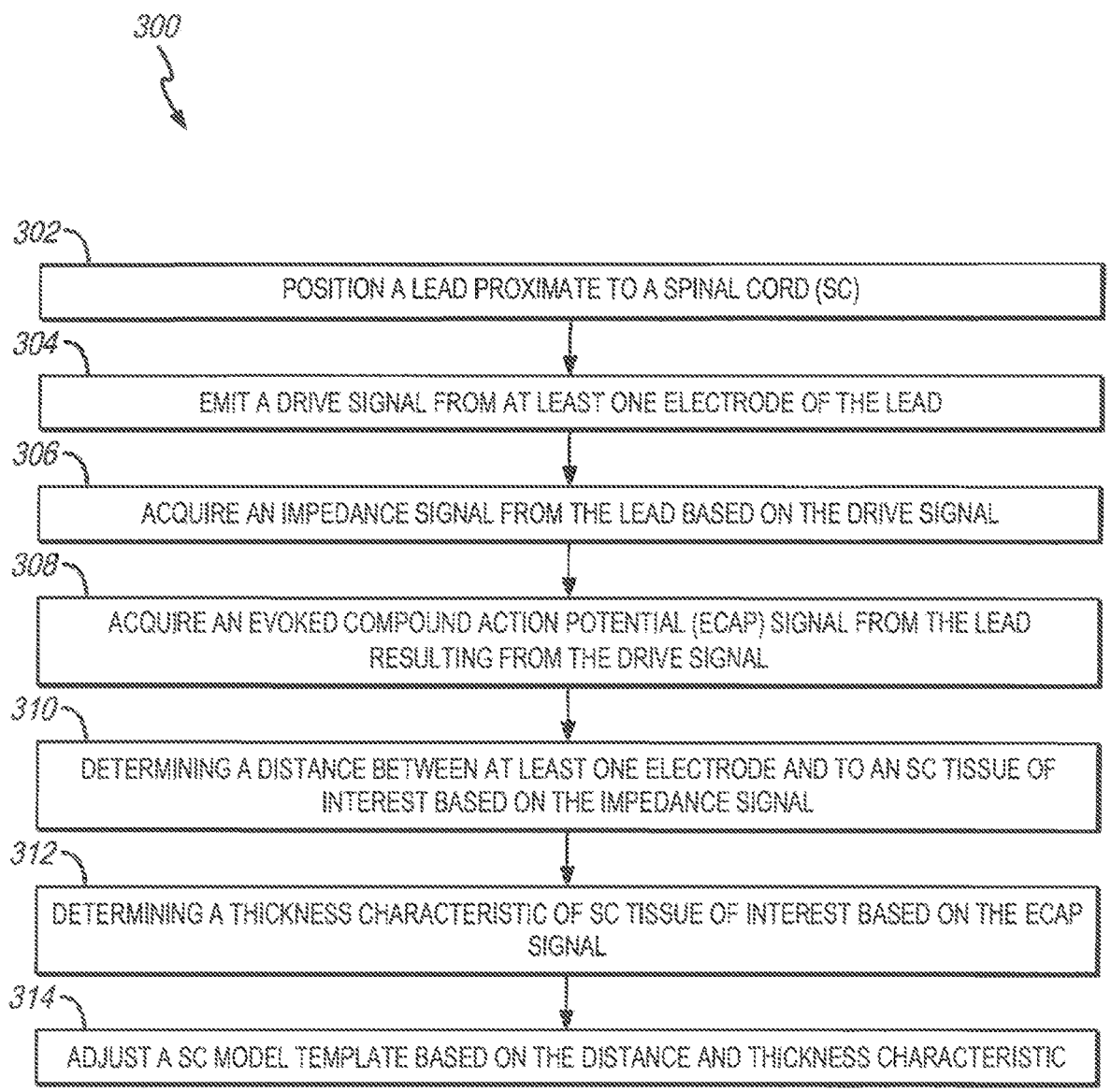
FIG. 3 is a flowchart of a method for determining a patient-specific anatomical model based on impedance and evoked compound action potential.

FIG. 3 is a flowchart of a method 300 for determining a patient-specific anatomical model based on impedance and evoked compound action potential signals. The method 300 may employ one or more of the components 52-58 described above, for example, the component 52, the controller 251, the CPU 102, and/or the CPU 152. Optionally, the operation of the method 300 may represent actions to be performed by one or more circuits (e.g., the controller 251) that include or are connected with one or more processors, microprocessors, controller, microcontrollers, Application Specific Integrated Circuits (ASICs), Field-Programmable Gate Arrays (FPGAs), or other logic-based devices that operate using instructions stored in a tangible and non-transitory computer readable medium (e.g., a computer hard-drive, ROM, RAM, EEPROM, flash drive, and/or the like), such as software, and/or that operate based on instructions that are hardwired into the logic of the one or more circuits. For example, the operations of the method 300 may represent actions of or performed by one or more processors when executing programmed instructions stored in a tangible and non-transitory computer readable medium.

In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. Furthermore, it is noted that the following is just one possible method of determining a patient-specific anatomical model based on impedance and evoked compound action potential. It should be noted, other methods may be used, in accordance with embodiments herein.

One or more methods may (i) acquire impedance and evoked compound action potential (ECAP) signals from a lead positioned proximate to a spinal cord (SC) and (ii) determine a patient-specific anatomical model based on the impedance and ECAP signals.

Figure 4:
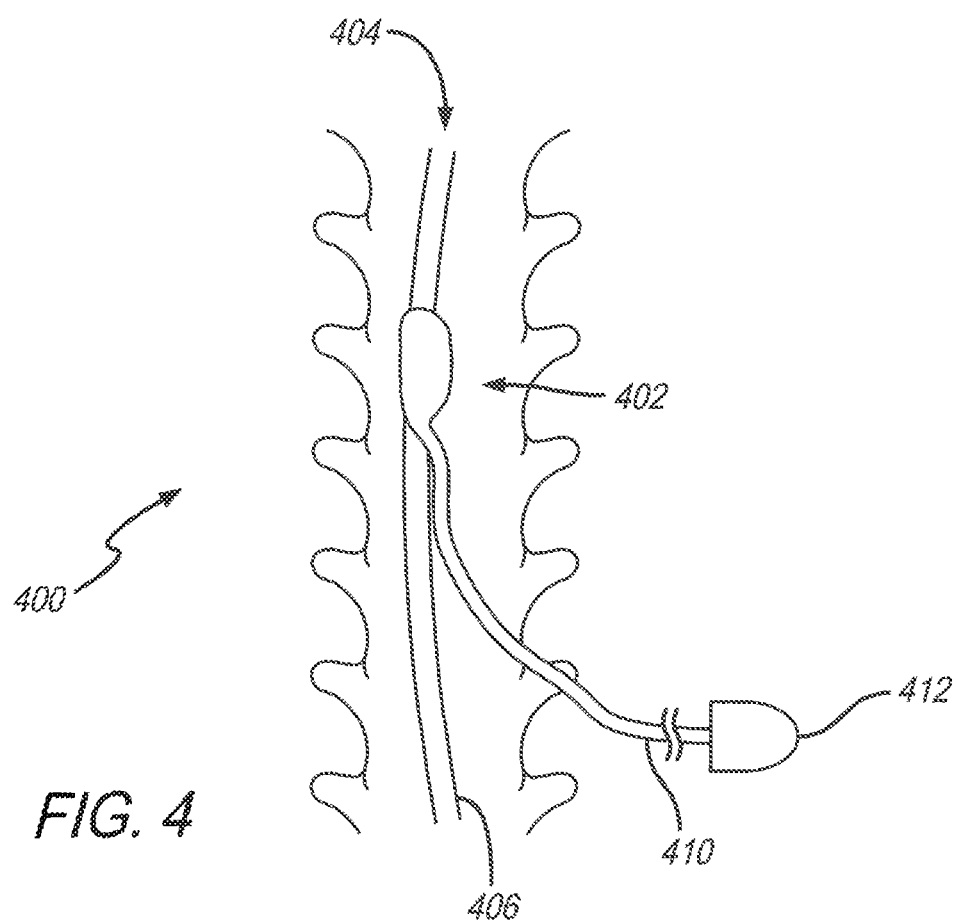
FIG. 4 illustrates a lead positioned proximate to a spinal cord, in accordance with an embodiment of the present disclosure.
Figure 5:
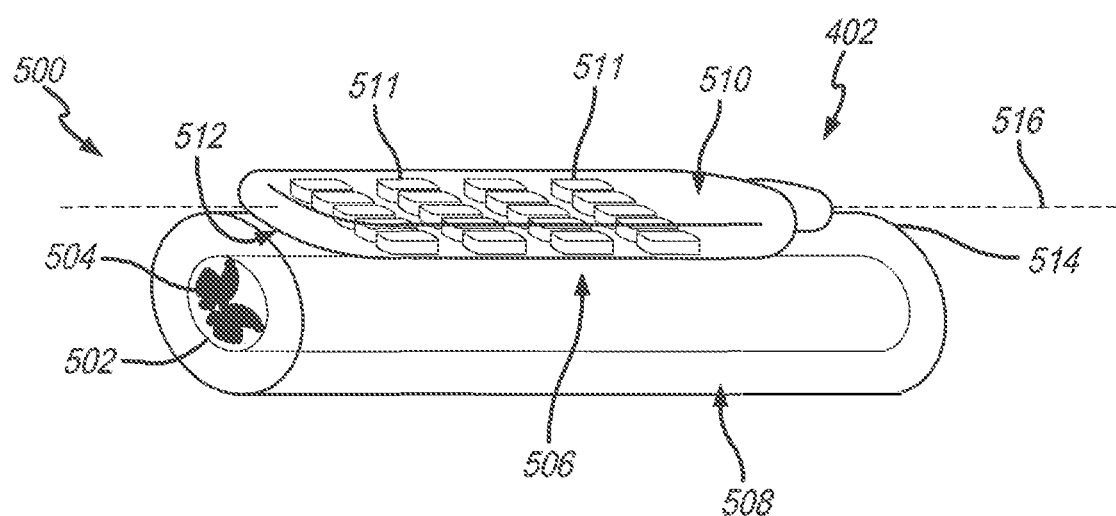
FIG. 5 illustrates a lateral view of the lead positioned proximate to the spinal cord of FIG. 4.

Beginning at 302, a lead 402 (shown in FIG. 4) is positioned proximate to a SC 406. The lead may be similar to the lead 210 with the paddle structure 214 depicted in FIG. 2 or may include other features, such as those described or referenced herein. FIG. 4 is an illustration of a lead placement 400, and FIG. 5 is an illustration of a lateral view 500 of the lead placement 400. The lead 402 includes an array of electrodes 511 overlaid on a front surface 512 of a paddle structure 510, and adjacent to the SC 406, or specifically, a dura layer 514 of the SC 406 positioned lengthwise along an axis 516. It should be noted that in other embodiments the electrodes 511 may not be a part of the paddle structure 510, such as, the percutaneous lead structure as described above. The lead 402 is positioned at a target position, in an epidural space 404 of a patient so as to be in close proximity to a nerve tissue of interest, the SC 406. For example, the position of the lead 402 enables one or more of the electrodes 511 to detect and/or measure an impedance and/or an ECAP generated by the corresponding neurons of the stimulation target in response to a drive signal emitted by one or more of the electrodes 511. The stimulation target may include afferent or sensory nerve fibers, such as Aβ sensory fibers, Aδ sensory fibers, C sensory fibers, and/or interneurons.

The lead 402 is connected via a lead body 410 to an IPG 412 (e.g., the IPG 250). Optionally, the lead 402 may be positioned at a selected vertebral level, which may be used to select an SC model template, as further described herein. FIG. 5 also depicts SC tissue within the dura layer 514, such as a dorsal column (DC) 506, white matter 502, grey matter 504, and cerebral spinal fluid 508.

At 304, a drive signal is emitted from at least one electrode 511 of the lead 402. For example, the drive signal may be generated from the IPG 412, such as from generating circuitry (e.g., the generating circuitry 252), and conducted to at least one of the electrodes 511 via switching circuitry (e.g., the switching circuitry 257) and the lead 402. The drive signal may represent a current pulse (e.g., a monophasic pulse) or a series of current pulses (e.g., a biphasic pulse, tri-phasic pulses), a sinusoidal waveform, a burst waveform, and/or the like which are emitted from at least one of the electrodes 511 with a predetermined amplitude and pulse width. Additionally, or alternatively the drive signal may be a voltage pulse with a predetermined amplitude and pulse width. The drive signal is used by the IPG (e.g., IPG 412, IPG 250) and/or the system 100 to determine anatomical parameters of interest (e.g., CSF thickness) and landmark locations (e.g., position of the electrodes 511 with respect to SC tissue of interest) of the SC based on impedance (at 306) and ECAP signals (at 308) resulting from the drive signal. Additionally, or alternatively, in connection with FIG. 26, the drive signal may correspond to a stimulation waveform and be used by the IPG to determine neural tissue damage, changes in the substrate (e.g., composition within the DC 506), movement of the lead 210, and/or the like.

Optionally, the drive signal may be a series of pulses. At least one subset of the series of pulses may be shaped (e.g., pulse width, amplitude, frequency) to facilitate measurement of the impedance signal. Additionally, or alternatively, at least another subset of the series of pulses may be shaped to facilitate measurement of the ECAP signal. It should be noted that in at least one embodiment the drive signal may be shaped to facility measurement of both the impedance signal and the ECAP signal.

At 306, an impedance signal is acquired from the lead based on the drive signal. The magnitude of the impedance signal is based on electrical properties, such as the conductivity, of the SC tissue proximate to the electrode(s) emitting the drive signal and/or acquiring the impedance signal. For example, if the proximate SC tissue is primarily epidural fat the impedance signal will have a high magnitude due to the low conductivity of epidural fat. In another example, if the proximate SC tissue is primarily CSF the impedance signal will have a low magnitude due to the high conductivity of the CSF. The impedance signal may be measured and stored in the memory 261. Based on the impedance signals, the system 100 and/or controller 251 may determine the electrical conductivity of the CSF and/or epidural fat layer of the SC tissue.

The impedance signal may correspond to a discrete impedance value or a calculated impedance over time during the drive signal. For example, the drive signal may be a current pulse emitted from two or more electrodes 511 (e.g., one electrode is in a cathode state, one electrode is in an anode state). Alternatively, the drive signal may be emitted from at least one of the electrodes 511 and the housing (e.g., the can 259). A voltage may be measured from the two or more electrodes 511 delivering the drive signal by the sensing circuitry 258 and/or the controller 251 comparing the two voltage potentials of the two or more electrodes 511 during the drive signal. Additionally, or alternatively, the voltage may be measured by one or more alternative electrodes 511 (e.g., not emitting the drive pule) during the drive signal and received by the sensing circuitry 258. Using the measured voltage and the drive signal, the controller 251 can determine the impedance signal (variable $Z_c$), using Equation 1, by dividing the measured voltage (variable $V_{measured}$) by the known stimulation current (variable $I_{stim}$) for the drive signal.

$$Z_c = V_{measured}/I_{stim} \qquad \text{(Equation 1)}$$

In another example, the drive signal may be a voltage pulse emitted from two or more electrodes 511. Alternatively, the drive signal may be emitted from at least one of the electrodes 511 and the housing (e.g., the can 259). A measured current may be measured from the at least one electrode 511 emitting the drive signal or by an alternative electrode 511 (e.g., not emitting the drive signal) during the drive signal, and received by the sensing circuitry 258. Using the measured current and the known stimulation voltage value for the drive signal, the controller 251 can determine the impedance signal (variable $Z_c$) using, Equation 2, by dividing the stimulation voltage (variable $V_{stim}$) of the drive signal by the measured current (variable (measured).

$$Z_c = V_{stim}/I_{measured} \qquad \text{(Equation 2)}$$

It should be noted in various embodiments, one or more of the electrodes 511 may be used for emitting a stimulation waveform (e.g., the drive signal) and measuring of the impedance signal (or ECAP signal at 308 generated by the corresponding neurons of the stimulation target). Additionally, or alternatively, a subset of the electrodes 511 may be used for emitting the drive signal and another subset of the electrodes 511 may be used to measure the impedance signal (or ECAP signal at 308).

Figure 6:
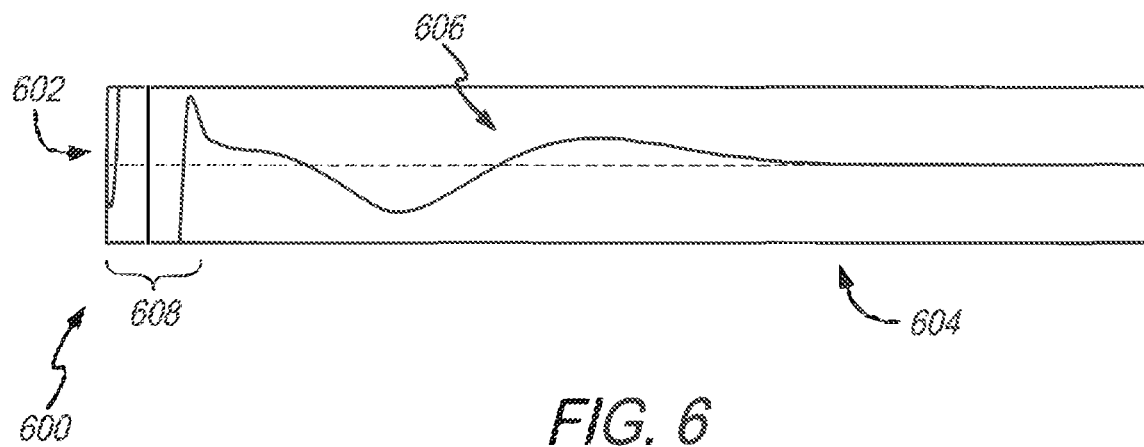
FIG. 6 illustrates a graphical representation of electrical potential measurements at an electrode from the lead in FIG. 4.

Returning to FIG. 3, at 308, the method 300 acquires an ECAP signal from the lead 402 resulting from and/or induced by the drive signal. FIG. 6 illustrates a graphical representation 600 of an ECAP signal measured at one or more of the electrodes 511 from the lead 402 during and after the measurement pulse. A horizontal axis 604 represents time, and a vertical axis 602 represents an electrical potential magnitude of the ECAP signal measured at the electrode 511. The ECAP signal may include a stimulation induced artifact component 608 and an ECAP waveform 606. The component 608 is an electrical artifact in the sensed ECAP signal due to the measurement pulse delivered by the electrode 511. The controller 251 and/or sensing circuitry 158 may filter out the component 608 by automatically adjusting the gain concurrently when the drive signal(s) are delivered to the electrodes 511. An ECAP waveform 606 is measured utilizing the electrode 511 by the sensing circuitry 158.

Figure 7:
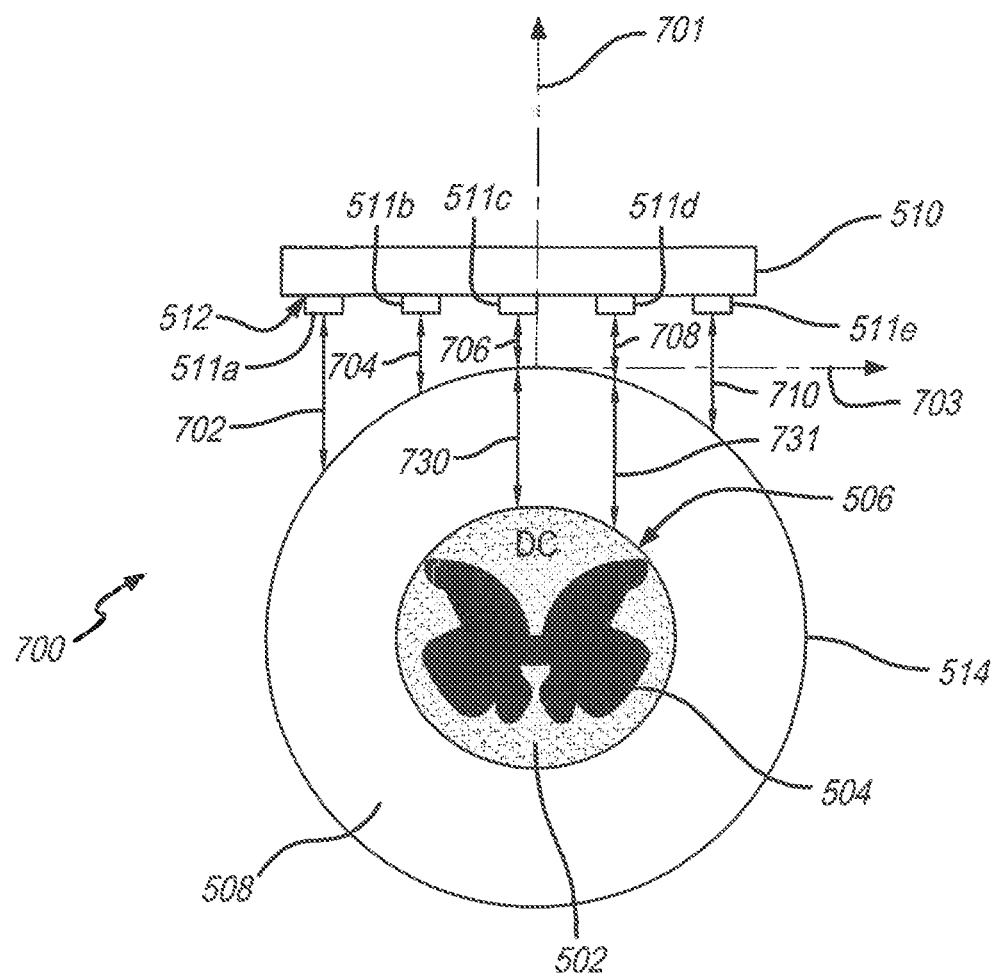
FIG. 7 illustrates a two dimensional cross section of the lead and spinal cord of FIG. 4.
Figure 8:
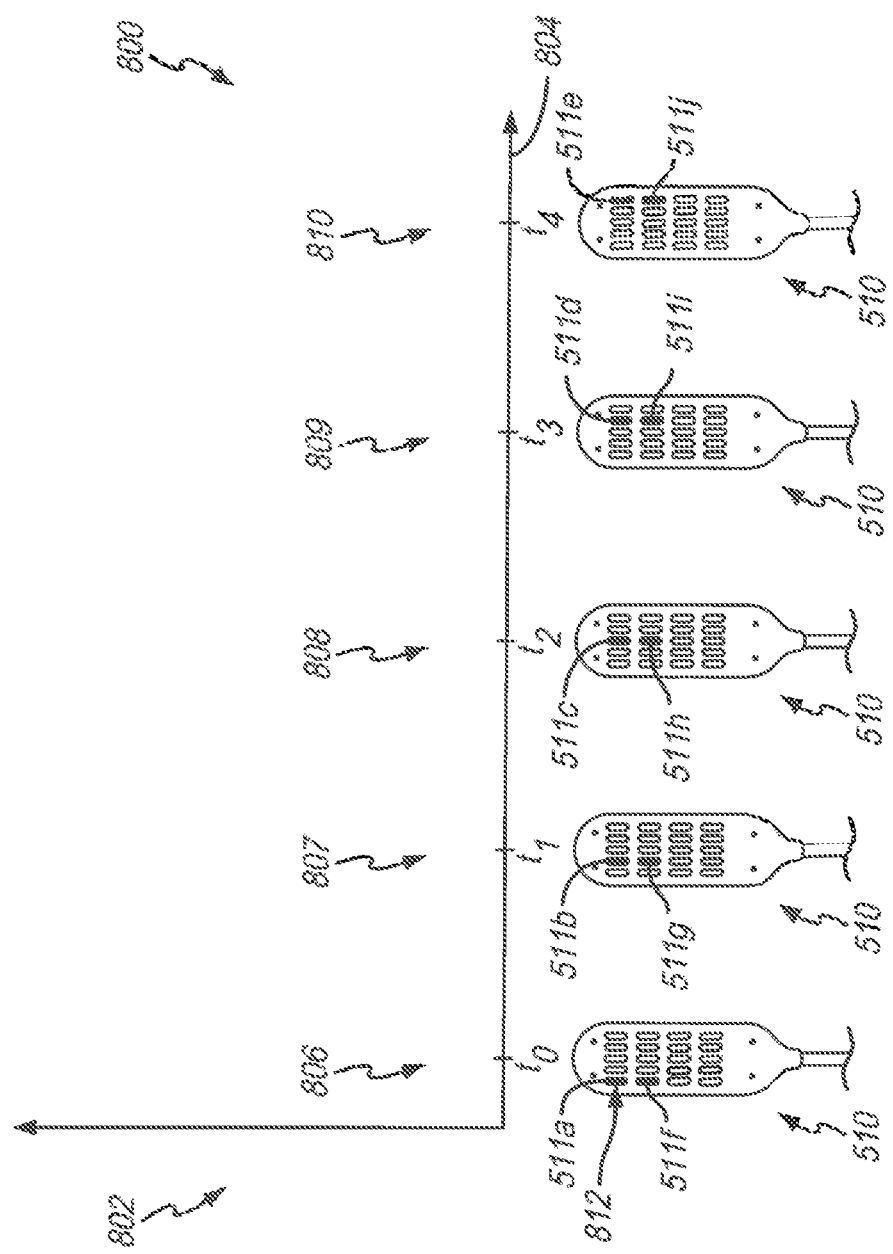
FIG. 8 is a graphical illustration of impedance measurements from the lead corresponding to a position of the lead relative to the spinal cord tissue of FIG. 7.

At 310, a distance (e.g., 702-710) between the at least one electrode and a SC tissue of interest is determined based on the impedance signal. The determination at 310 is further described in connection with FIGS. 7 and 8. FIG. 7 illustrates a two dimensional (2D) cross-sectional view 700 of the paddle structure 510 of the lead 402 and spinal cord 406 from FIG. 4 at a row 812 (FIG. 8) of the electrodes 511a-e. FIG. 8 is a graphical illustration 800 of the impedance signals 806-810 corresponding to drive signals originating or sensed from electrodes 511a-e, acquired at 304, at different points in time.

The electrodes 511a-e are each a distance 702-710, respectively, away from the dura layer 514 surrounding the CSF 508. At different points in time (e.g., t0, t1, t2, t3, t4) a corresponding electrode 511a-e emits the drive signal (e.g., a monophasic current pulse), and a corresponding electrode 511f-j senses an electrical response (e.g., sensed voltage, sensed current) in response to the drive signal for the impedance signal. It should be noted that in other embodiments, the electrode sensing the electrical response and emitting the drive signal may be interchanged (e.g., electrode 511f emits the drive signal, electrode 511a senses the electrical response), located in different columns on the electrode array 511, or measured from the same electrodes (e.g., electrode 511a-e) emitting the drive signal. Optionally, more than one electrode may sense the electrical response. Additionally, or alternatively, the same electrode may sense the electrical response for more than one electrode emitting the drive signal. Optionally, more than one electrode may emit the drive signal (e.g., bi-phasic pulse, tri-phasic pulse).

The impedance signal is plotted on the graphical illustration 800. A vertical axis 802 represents magnitude (e.g., ohms), and the horizontal axis 804 is time. The impedance signal 806 corresponds to a drive signal emitted from the electrode 511a, the impedance signal 807 corresponds to a drive signal emitted from the electrode 511*b*, the impedance signal 808 corresponds to a drive signal emitted from the electrode 511*c*, the impedance signal 809 corresponds to a drive signal emitted from the electrode 511*d*, the impedance signal 810 corresponds to a drive signal emitted from the electrode 511*e*.

The magnitude of the impedance signal 806-810 corresponds to a distance (e.g., 702-710) from the emitting electrode (e.g., 511*a-e*) to the dura layer 514 or CSF 508. For example, larger distances (e.g., 702, 710) yield a larger impedance (e.g., 806, 810) because the lead is further from the highly conductive CSF 508. Alternatively, relatively smaller distances (e.g., 706) yield a comparatively smaller impedance (e.g., 808) since the lead is closer to the highly conductive CSF 508.

The impedance signals 806-810 may be compared by the system 100 and/or the controller 251 to an impedance distance database to determine the distances 702-710. The impedance distance database may be stored in memory (e.g., memory 261, ROM 104, RAM 106, a hard drive 108) and based on traditional three dimensional electromagnetic computation simulations or priori information of experimentally measured impedance measurements and electrode positioned across a patient population. The impedance distance database includes a collection of candidate impedances with associated distances. The impedance distance database may be used as a look up table to match a corresponding impedance signal magnitude with a distance. Additionally, the values of the distances and/or corresponding impedance signals magnitudes of the impedance distance database may be dependent on the structure of the lead 402 and the electrodes 511. For example, the impedance distance database may have different sets of values of the distances. A first set of distance values correspond to impedance signals for the paddle structure 510, and a second set of distance values for another structure where the electrodes 511 are in the shape of a ring such that each electrode 511 continuously covers the circumference of the exterior surface of the lead 402. It should be noted that the impedance distance database may have more than two sets of values of the distances with corresponding impedance signal magnitudes for various other electrode 511 and/or lead 402 structures as described herein.

In at least one embodiment, for each impedance signal 806-810, the system 100 and/or the controller 251 may find a matching impedance signal magnitude in the impedance distance database (or interpolation with closest data points) with a corresponding distance from an electrode contact to the dura layer 514 or CSF 508. For example, the system 100 may compare the impedance signal magnitude for the impedance signal 808 to the impedance distance database. The impedance distance database may list the impedance magnitude with a corresponding distance of 0.2 mm. Based on the listed distance, the system 100 may determine that the distance 706 is 0.2 mm from the electrode 511*c* to the SC tissue of interest (e.g., the dura layer 514).

Based on the combination of distances 704-710, the system 100 may determine an overall position of the paddle based on y and x axes 701 and 703 centered proximate to the paddle 510 on the SC tissue of interest. Optionally, the x and y axes 703, 701 may be centered on one of the electrodes, for example, the center column electrode, the electrode 511*c*, on the paddle structure. The y axis 701 corresponds to a dorsal/ventral position (e.g., dorsal position is based away from the x axis 703, ventral position is based towards the x axis 703), for example, based from the distances 702-710. The x axis 703 corresponds to a medial/lateral position (e.g., medial position is on the y axis 701, lateral position is based away from the y axis 701 in either a left or right direction along the x axis 703).

Figure 9:
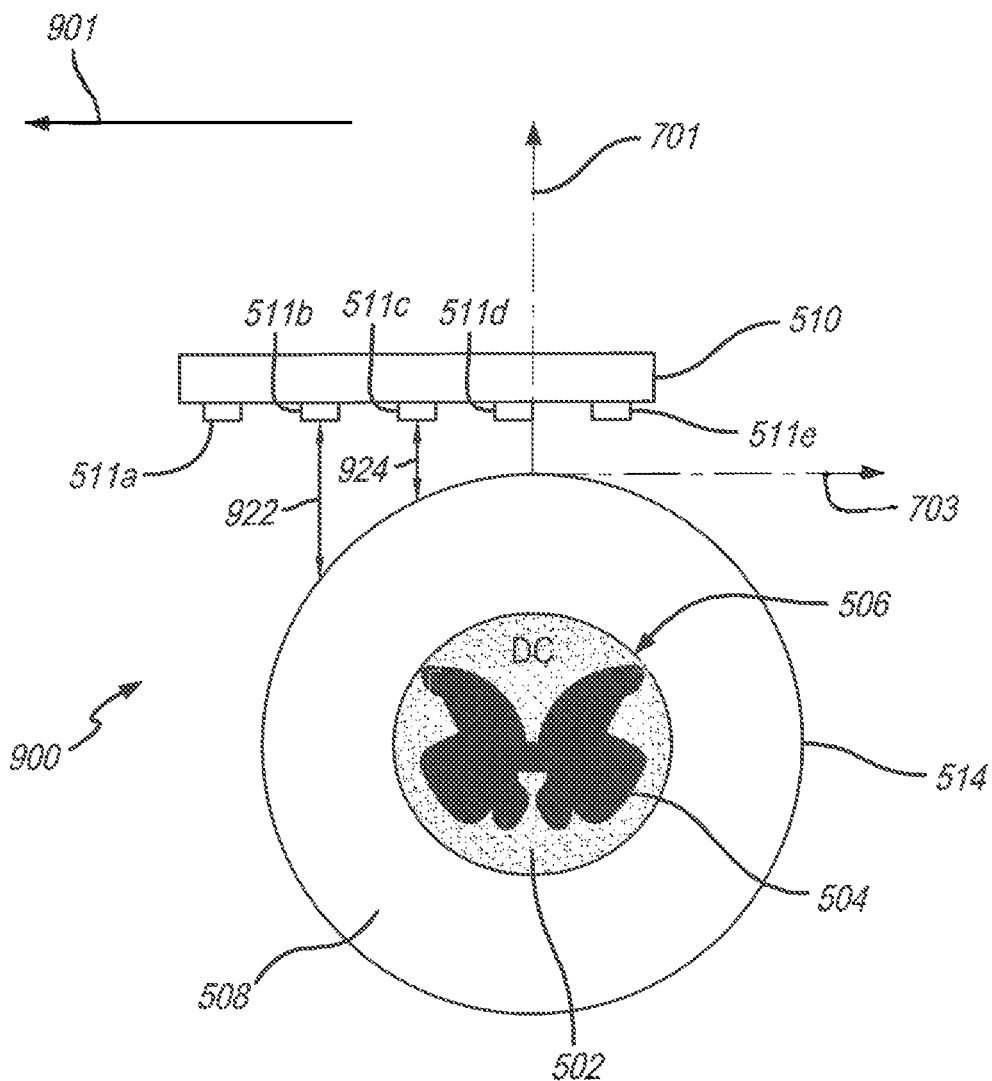
FIG. 9 illustrates a two dimensional cross section of the lead and spinal cord of FIG. 4.

For example, the system 100 and/or the controller 251 may determine the medial/lateral position of the paddle structure 510 based on an interrelation of the magnitude of the impedance signals or morphology (e.g., changes in slope, peaks, rising/falling edges) of a line graph (e.g., an impedance curve 1220) formed from the impedance signals as further described in connection to FIGS. 9 and 10. FIG. 9 illustrates a two dimensional (2D) cross section 900 of the paddle structure 510. The paddle structure 510 is in a laterally shifted position (e.g., left lateral) along the x axis 703 with respect to the SC tissue of interest (e.g., the CSF 508, the dura layer 514) relative to the paddle structure 510 shown in FIG. 7, in the lateral direction of an arrow 901. Based on the shifted position, a first peripheral column or portion of the electrodes (e.g., the column of the electrodes at 511*a*) will be located remotely from the SC tissue of interest, while an opposite second peripheral column or portion of the electrodes (the column at electrode 511*e*) is located proximate to the SC tissue of interest.

Figure 10:
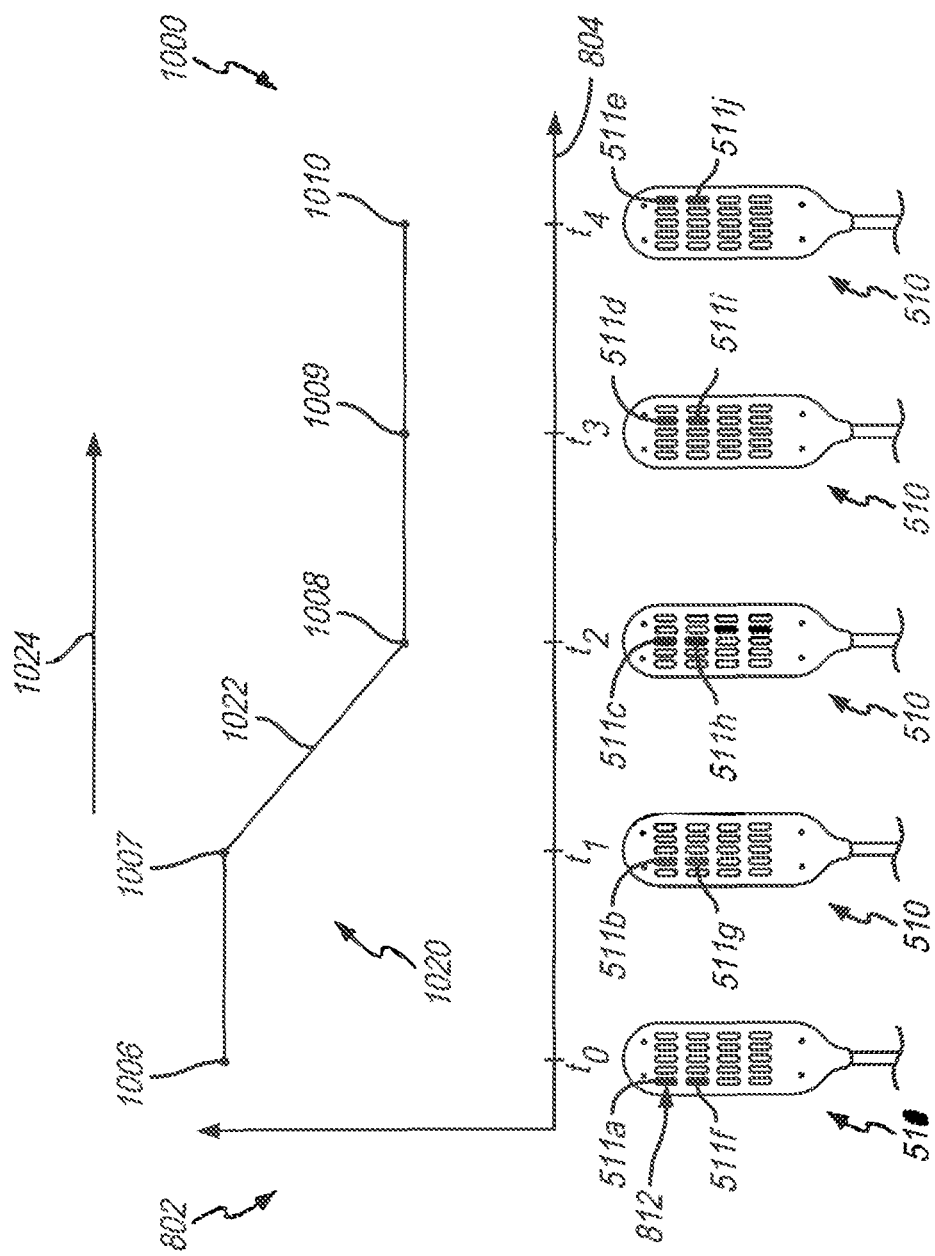
FIG. 10 is a graphical illustration of impedance measurements from the lead corresponding to a position of the lead relative to the spinal cord tissue of FIG. 9.

FIG. 10 is a graphical illustration 1000 of the impedance signals 1006-1010 corresponding to drive signals originating from electrodes 511*a-e* of a row 812 of the paddle structure 510 (e.g., acquired at 304), at different points in time. The impedance signals 1006-1010 may form an impedance curve 1020. It should be noted that the magnitude of the impedance signals 1006-1007 are approximately the same, and the magnitude of the impedance signals 1008-1010 are also approximately the same. The shifted position of the paddle structure 510 causes a falling edge (e.g., change) 1022 between the impedance signals 1007 and 1008, such that the magnitude of the impedance signal 1008 is lower relative to the magnitude of the impedance signal 1007. The falling edge 1022 corresponds to the change in distances 924 and 922, specifically a decrease in distance, respectively, of the electrodes 511*b-c* with respect to the SC tissue of interest (e.g., dura layer 514 and/or CSF 508) in the direction of an arrow 1024. Conversely, a rising edge, in the direction of the arrow 1024, may correspond to an increase in distance.

Based on the falling edge 1022 and the interrelation of the magnitudes of the impedance signals 1006-1007 and 1008-1010 being approximately the same, respectively, the system 100 and/or the controller 251 may determine that the falling edge 1022 corresponds to a portion of the paddle structure 510, such as electrodes 511*a-b*, is located remotely from the SC tissue of interest. Since the falling edge 1022 decreases in magnitude in the direction of the arrow 1024, the system 100 and/or the controller 251 can determine that the paddle structure 510 is shifted laterally.

Figure 11:
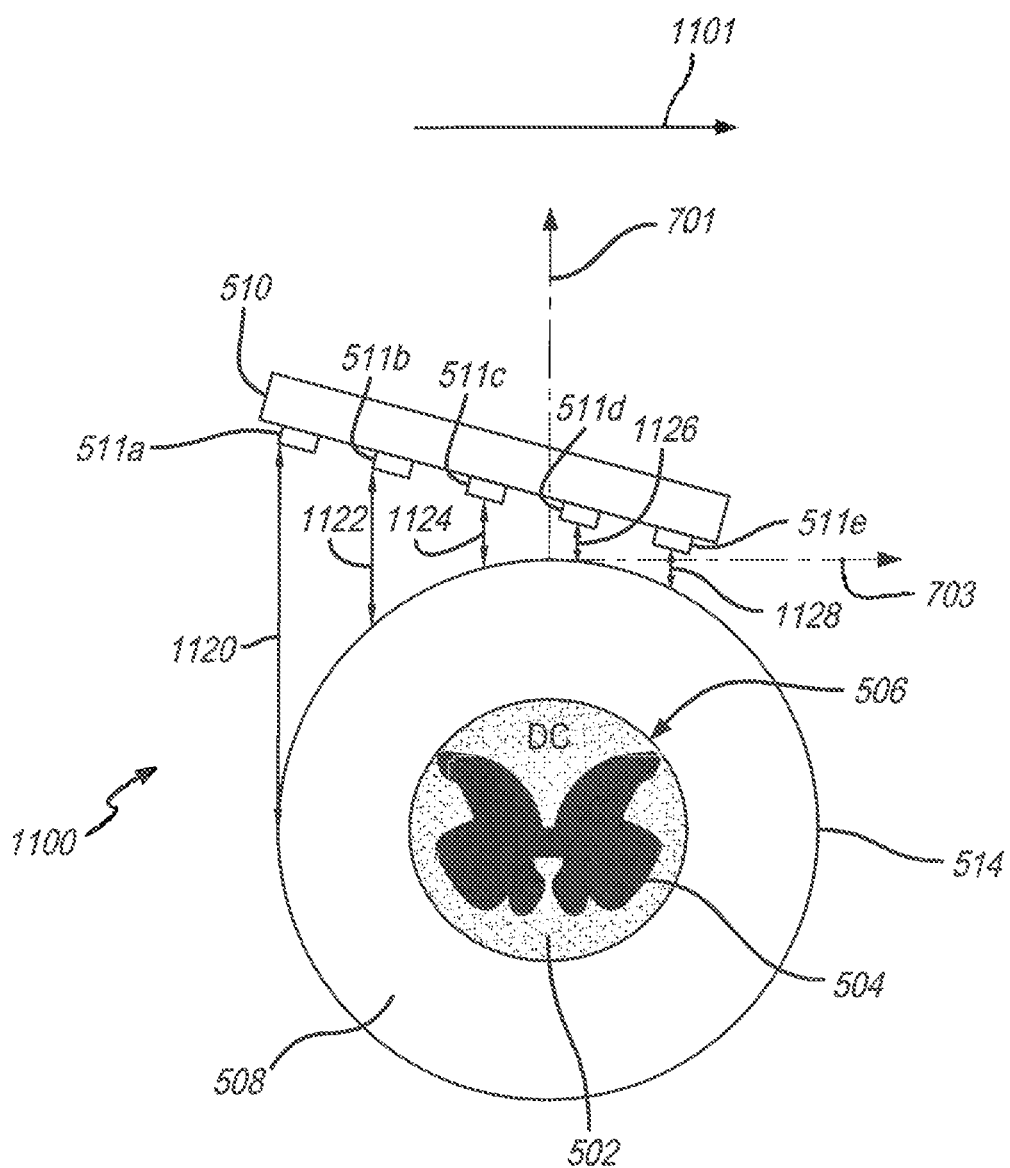
FIG. 11 illustrates a two dimensional cross section of the lead and spinal cord of FIG. 4.

Additionally, based on the combination of distances of the electrodes 511 from the SC tissue of interest, the system 100 and/or the controller 251 can determine an angle of the paddle structure 510 relative to the SC tissue of interest. For example, the system 100 and/or controller 251 may determine that the paddle structure 510 is positioned at an angle based on a slope of an impedance curve 1220, as described further in connection to FIGS. 11 and 12. FIG. 11 illustrates a two dimensional (2D) cross section 1100 of the paddle structure 510. The paddle structure 510 is in an angled position relative to the axes 701 and 703 with respect to the SC tissue of interest (e.g., the CSF 508, the dura layer 514). Based on the angle of the paddle structure 510, a first peripheral column or portion of the electrodes (e.g., the column of the electrodes at 511*a*) is located remotely from the SC tissue of interest, while an opposite second peripheral column or portion of the electrodes (the column at the electrodes 511e) is located proximate to the SC tissue of interest. Specifically, the first peripheral column is dorsally position to the second peripheral column relative to the SC tissue of interest. Based on the angle, each subsequent distance 1120-1128 of the electrodes 511a-e from the SC tissue of interest (e.g., dura layer 514 and/or the CSF 508), in the direction of an arrow 1101, decreases, respectively, at an approximate rate.

Figure 12:
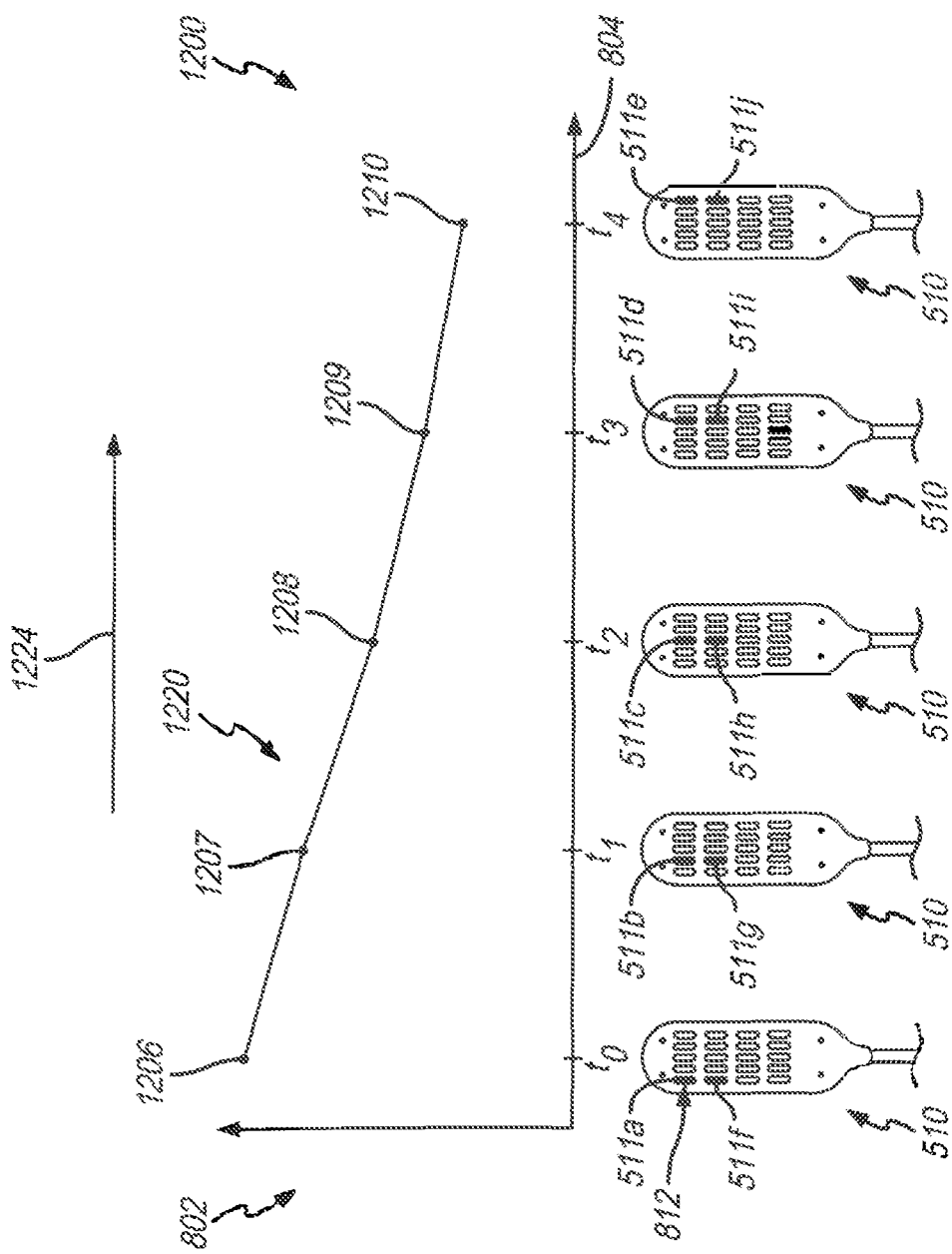
FIG. 12 is a graphical illustration of impedance measurements from the lead corresponding to a position of the lead relative to the spinal cord tissue of FIG. 11.

FIG. 12 is a graphical illustration 1200 of the impedance signals 1206-1210 corresponding to drive signals originating from electrodes 511a-e of the row 812 of the paddle structure 510 (e.g., acquired at 304), at different points in time. The impedance signals 1206-1210 form an impedance curve 1220. The decreasing rate of the distances 1120-1128, based on the angle of the paddle structure 510, results in an overall decreasing slope in the impedance curve 1220 across the impedance signals 1206-1210 in the direction of an arrow 1224. The overall decreasing slope may be detected by the system 100 and/or the controller 251, and used to determine that the paddle structure 510 is positioned at an angle with respect to the SC tissue of interest (e.g., the dura layer 514, the CSF 508).

Figure 13:
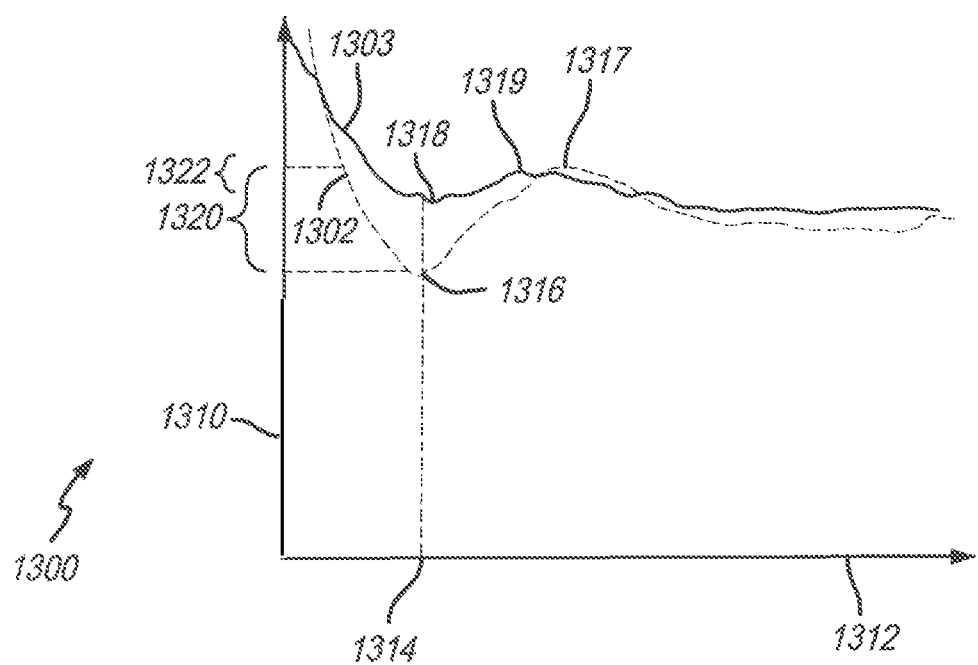
FIG. 13 is a graphical representation of evoked compound action potential signals resulting from a drive signals, according to an embodiment of the present disclosure.

Returning to FIG. 3, at 312, a thickness characteristic of the SC tissue of interest is determined based on the ECAP signal. For example, the thickness characteristic may be a CSF thickness 730, 731 (e.g., a distance from the dura layer 514 to the DC 506). FIG. 13 illustrates a graphical representation 1300 of ECAP signals 1302-1303 resulting from the drive signal from the electrodes 711c-d, respectively. A horizontal axis 1312 represents time, and a vertical axis 1310 represents the amplitude of the measured EP. Morphology characteristic (e.g., peak amplitude, width, latency, duration, descending and ascending slopes) of the ECAP signals 1302, 1303 may be dependent on the thickness characteristic of the SC tissue of interest, such as the CSF thickness 730-731 (FIG. 7). For example, the ECAP signals 1302 and 1303 each result from two different locations of electrodes 711c-d emitting drive signals with respect to the CSF thickness 730 and 731, respectively. The signals 1302 and 1303 also include, at time 1314, a minimum peak 1316 and 1318 at time 1314 and a maximum peak 1317 and 1319 from the ECAP signals with different peak to peak magnitudes 1320 and 1322, respectively. Generally, greater CSF thickness will be correlated to lower ECAP peak to peak magnitudes, since the lead is further from the neural fiber population.

The system 100 and/or the controller 251 may compare one or more ECAP signals features representing the morphology of the ECAP signal 802 such as a slope, a maximum and/or minimum amplitude, time delay from onset of stimulation to peak ECAP amplitude, or the like, with an ECAP database to determine the thickness characteristic of the SC tissue of interest at or near the corresponding electrode (e.g., the electrode 711c-d). Based on the combination of thickness measurements for each electrode, the system 100 and/or the controller 251 can determine an overall thickness of the SC tissue of interest. The ECAP database may be stored in memory (e.g., memory 261, ROM 104, RAM 106, a hard drive 108) and based on traditional three dimensional electromagnetic computation simulations or priori information of experimentally measured ECAP signals and electrode positioned across a patient population. The ECAP database includes a collection of candidate ECAP signal features with associated thickness characteristics of the SC tissue of interest. The ECAP database may be used as a look up table to match one or more ECAP signal features with thickness characteristic of SC tissue of interest.

In at least one embodiment, a peak to peak 1320 measurement from the ECAP signal 1302 may be measured by the system 100 and/or the controller 251, and compared with the ECAP database to find a matching peak to peak ECAP signal in the ECAP database (or interpolation with closest data points) with a corresponding CSF thickness. For example, the system 100 may compare the peak to peak 1320 to the ECAP database. The ECAP database may list a peak to peak matching the peak to peak 1320 with a corresponding CSF thickness of 2.8 mm. Based on the listed CSF thickness, the system 100 may determine that the CSF thickness 730 is 2.8 mm.

Figure 14:
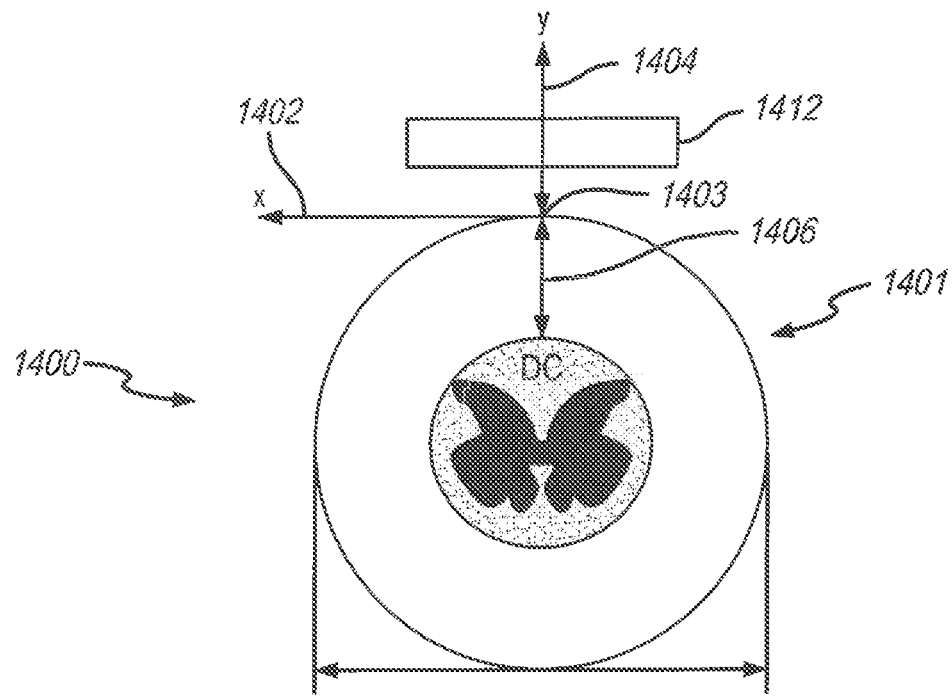
FIG. 14 is a graphical illustration of a spinal cord model template, according to an embodiment of the present disclosure.

At 314, the method 300 adjusts an SC model template 1400 based on the distance and thickness characteristic. FIG. 14 is a graphical illustration of a SC model template 1400. The SC model template 1400 may be selected from a SC model template database stored in memory (e.g., ROM 104, RAM 106, a hard drive 108) by the clinician using the system 100. Each of the SC model templates within the SC model template database may correspond to a vertebral level of the SC. For example, the clinician may select the vertebral level corresponding to a location of the lead 402, paddle structure 510, and/or one or more electrodes 511 using the system 100. Based on the vertebral level, the SC model template 1400 may be selected. Optionally, the SC model template may include a coordinate origin 1403 centered (e.g., along the x and y axes 1402, and 1404) relative to SC tissue 1401.

Figure 15:
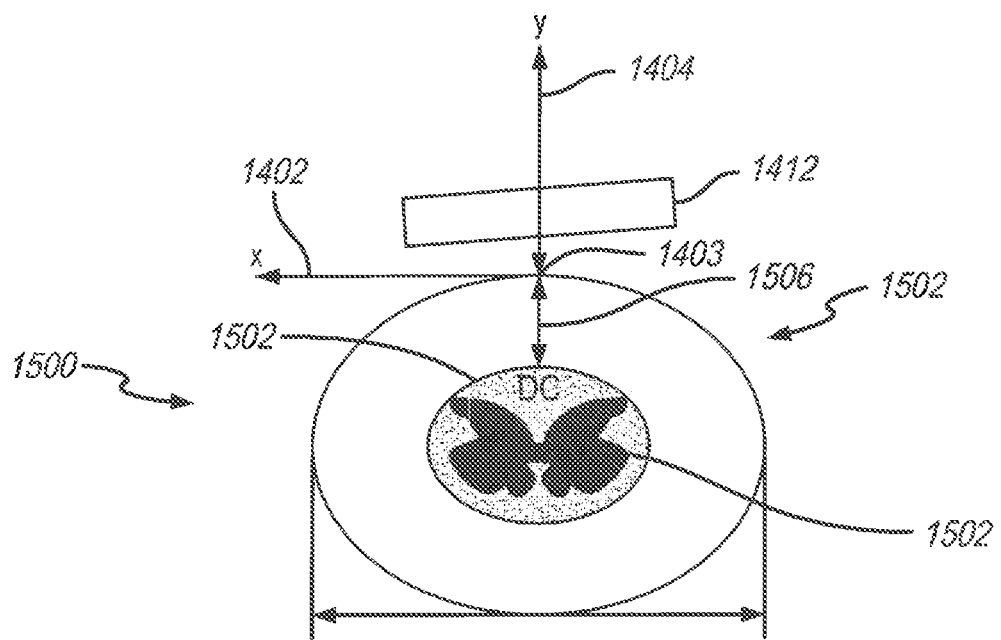
FIG. 15 is a graphical illustration of an adjusted spinal cord model template based on thickness and characteristic measurements of spinal cord tissue, according to an embodiment of the present disclosure.

After the selection of the SC model template 1400, the system 100 and/or the controller 251 may adjust the SC model template 1400 based on the distance and thickness characteristic operations determined at 310 and 312. FIG. 15 is a graphical illustration of an adjusted SC model template 1500. Based on the distance and thickness characteristic measurements, the system 100 and/or the controller 251 may determine ratios along the x and y axes 1402, 1404 to scale the SC model template 1400 resulting in the adjusted SC model template 1500, which represent the SC of the patient.

For example, the SC model template 1400 has a CSF thicknesses 1406 based on a position of a lead 1412. The thickness characteristic measurements determined at 312 correspond to CSF thicknesses 1506. The system 100 may determine a ratio along the x and y axes 1402, 1404 based on the CSF thicknesses 1506 compared with the CSF thicknesses 1406. The ratio is used to adjust the SC model template 1400 to form the adjusted SC model template 1500. The system 100 may further adjust the position (e.g., medial/lateral, distance from the dura layer, angle relative to the SC tissue) of the lead 1412 in the SC model template 1400. The position of the lead 1412 is adjusted based on the distance characteristics determined at 310 with respect to the adjusted SC model template 1500 to determine the adjusted position of the lead 1412.

Optionally, the SC model template 1400 may also be adjusted based on one or more medical images acquired by a medical imaging system (e.g., magnetic resonance imaging, computed tomography, X-ray, or the like). The one or more medical images of the patient may be imported by the method 300 for determination of patient anatomy and electrode position. For example, segmentation of pre-operative MRI could provide detailed information about SC tissue geometric structure. In another example, once the lead 402 is implanted within the patient, post-operative CT or X-ray may be used to acquire positions of the electrodes 511. In another example, for an MRI compatible SCS system, both SC anatomy and location of the electrodes 511 may be obtained from post-operative MRI.

The medical images may also be used for image-based calibration of the impedance distance and/or ECAP databases. For example, the system 100 and/or controller 251 may use the impedance signal for investigating SC tissue properties, such as the electrical conductivity of the CSF layer or of the epidural fat, to be used in building and/or updating the impedance distance database. In another example, the impedance distance database and/or ECAP database may be based on nominal values of tissue conductivity based on priori information. Based on the medical images, the impedance distance and ECAP signals corroborated with positioned information of the electrodes 511 and/or SC tissue properties are used for minor adjustment of conductivity away from these nominal values.

Additionally, or alternatively, additional impedance and ECAP signals may be acquired. Each set of impedance and ECAP signals may correspond to different patient postures or positions, such as sitting, standing, supine, or the like. For example, a first set of impedance signal(s) and ECAP signal(s) may be acquired by the sensing circuitry 258 while the patient is in a first position, such as in a sitting position. When the patient adjusts to a second position, such as a standing position, the second set of impedance and ECAP signals may be acquired and so on for all desired postures. It should be noted that in other embodiments more than two different patient positions may be used. Optionally, the impedance and ECAP signals corresponding to multiple positions of the patient may be stored in a position measurement database on memory (e.g., memory 261, ROM 104, RAM 106, hard drive 108). Corresponding models (e.g., patient-specific anatomical models) at different postures may be built with associated changes in electrode location and SC anatomy. Through stimulation configurations with each patient-specific anatomical model, SCS programming guidance with each posture may be established and stored in the NS system 200 and/or the SCS programming guidance system 100.

A technical effect of acquiring impedance and ECAP signals at multiple positions allow the patient-specific anatomical model to be configured for different postures for SCS programming and stored in memory (e.g., ROM 104, RAM 106, hard drive 108). Allowing, patients to implement the desired SCS programming when using a graphical user interface of the system 100 when the posture or position of the patient changes.

Figure 16:
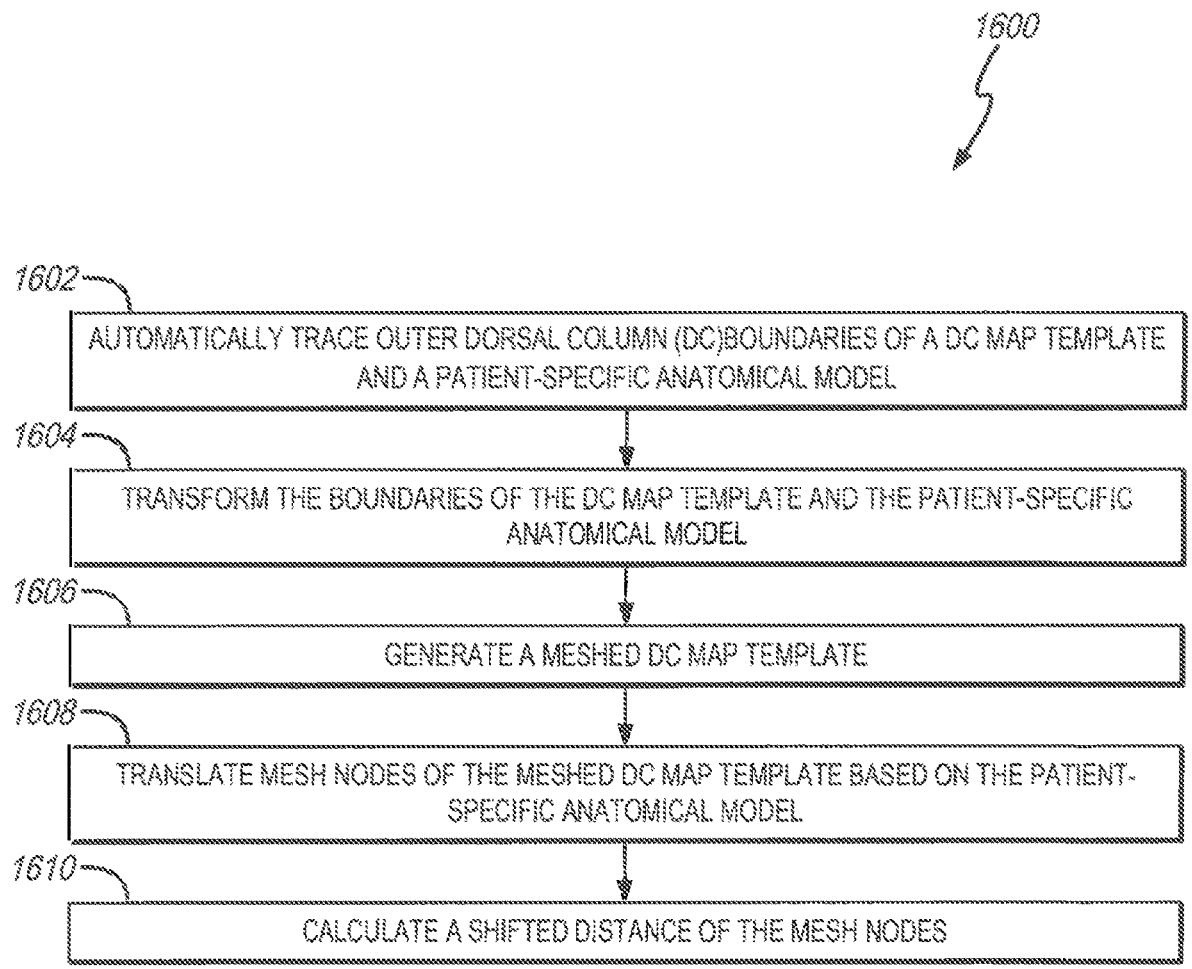
FIG. 16 is a flowchart of a method for transforming a dorsal column map template based on a dorsal column boundary of a patient-specific anatomical model, according to an embodiment of the present disclosure.

FIG. 16 is a flowchart of a method 1600 for transforming (e.g., morphing) a DC map template based on a DC boundary of the patient-specific anatomical model. The method 1600 may be employed by one or more of the components 52-58 described above, for example, the component 54. The method 1600 may employ structures or aspects of various embodiments (e.g., systems and/or methods) discussed herein. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. Furthermore, it is noted that the following is just one possible method of transforming a DC map template based on a DC boundary of the patient-specific anatomical model. It should be noted, other methods may be used, in accordance with embodiments herein.

A technical effect of the method 1600 is a transformed DC map template (e.g., a transformed DC map template 2000 of FIG. 20) that may be used to automatically identify which dermatomal zones are activated during SCS. Additionally, the transformed DC map template may be used to automatically calculate the area of activation or number of fibers activated in each zone. It should be noted although the method 1600 is described transforming a 2D DC map template, in at least one embodiment, a 3D DC map template may be transformed using the method 1600.

One or more methods may (i) generate a meshed DC map template and (ii) translate the mesh nodes of the meshed DC map template based on a patient-specific anatomical model.

Figure 17:
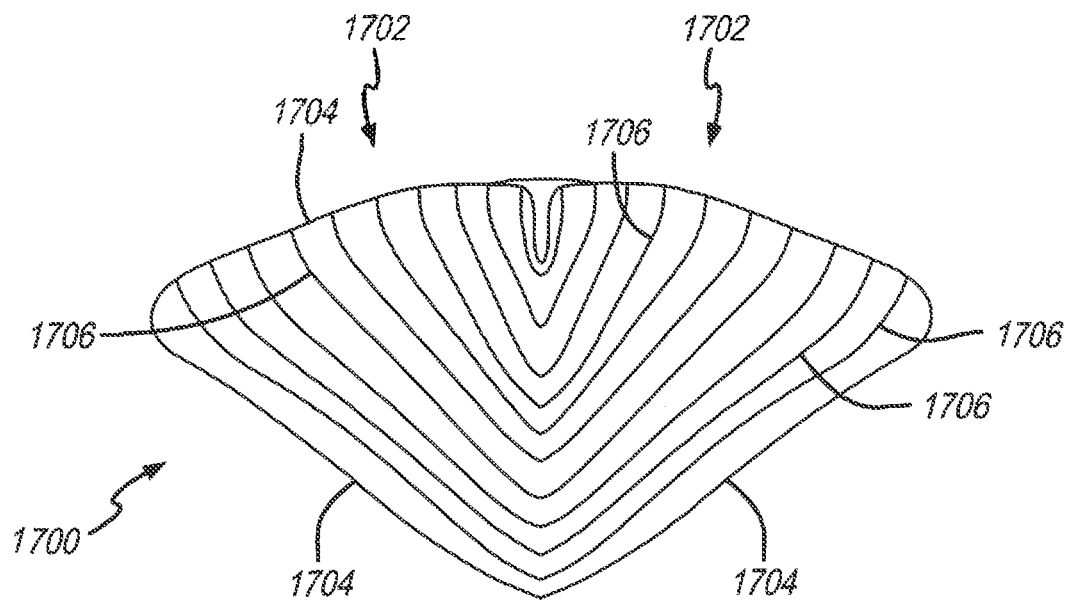
FIG. 17 is an illustration of a dorsal column map template, according to an embodiment of the present disclosure.

Beginning at 1602, the method 1600 automatically traces outer DC boundaries 1502 and 1704 of a DC map template (e.g., dermatomal zone map template is shown in FIG. 17) 1700 and a patient-specific anatomical model (e.g., the adjusted SC model template 1500). FIG. 17 is an illustration of the DC map template 1700. The DC map template 1700 includes dermatomal zones 1702 separated or bounded by internal zone boundaries 1706 and/or the DC boundary 1704. The system 100 may trace the outer DC boundaries 1502 and 1704 of the DC map template 1700 and the adjusted SC model template 1500.

At 1604, the method 1600 transforms the boundaries of the DC map template and the patient-specific anatomical model. The system 100 may translate and/or scale the DC boundaries 1502 and 1704 of the adjusted SC model template 1500 and the DC map template 1700 so each DC boundary 1502 and 1704 are overlapping. For example, the minimum and maximum value of the DC boundaries 1502 and 1704 along an x and y axes.

Figure 18:
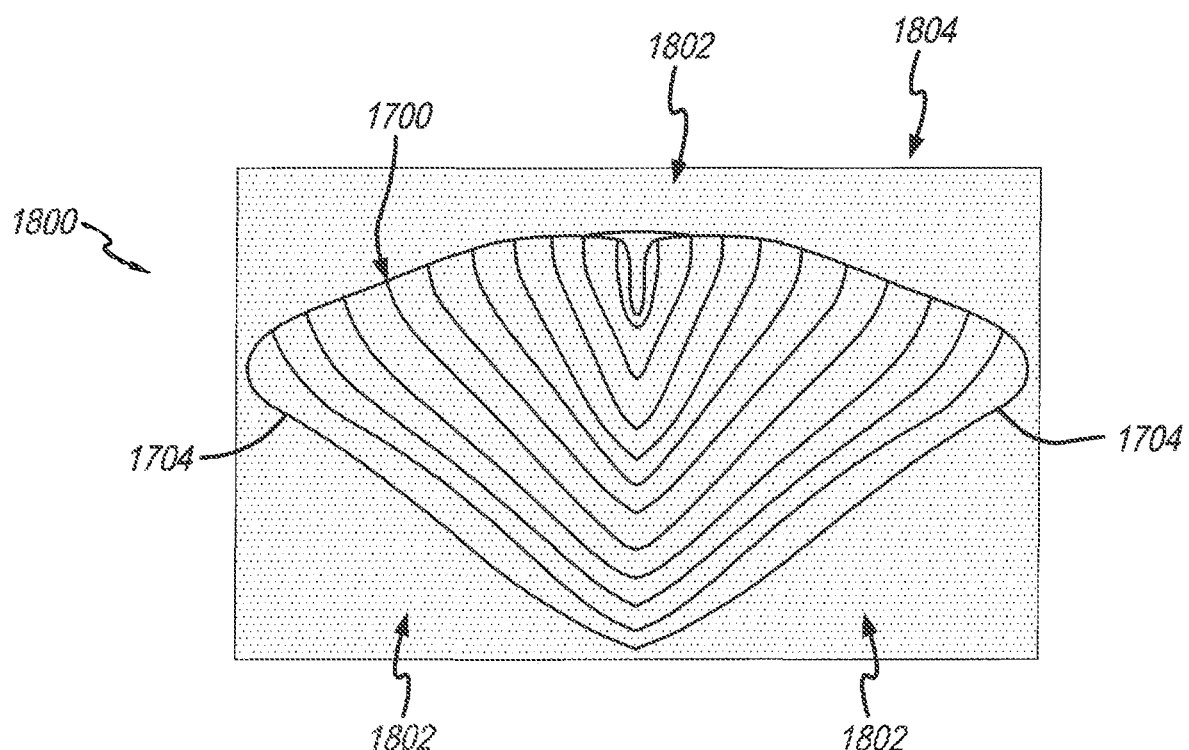
FIG. 18 is an illustration of a meshed dorsal column map template, according to an embodiment of the present disclosure.

At 1606, the method 1600 generates a meshed DC map template 1800. FIG. 18 illustrates the meshed DC map template 1800. The meshed DC map template 1800 includes the DC map template 1700 overlaid with a mesh 1804. The mesh 1804 is subdivided into multiple mesh nodes 1802 formed as a triangle. It should be noted that in other embodiments the mesh nodes 1802 may be formed as other shapes, for example, rectangles, parallelograms, or the like. The size of the mesh nodes 1802 may be based on a user-specified selection by the clinician using the system 100. It should be noted that in other embodiments the size and number of mesh nodes 1802 may be greater than or less than what is shown in FIG. 18. Optionally, the size and number of mesh nodes 1802 may be based on the computational limitations of the system 100. For example, if the system 100 has limited computational power, the size of the mesh nodes 1802 may increase (and the number of mesh nodes 1802 will decrease) to allow a predetermined amount of computational time needed at 1608.

At 1608, the method 1600 translates mesh nodes of the meshed DC map template based on the patient-specific anatomical model. The locations of the mesh nodes 1802 are shifted, as shown in FIG. 19, such that the mesh nodes 1802 lying on the DC boundary (e.g., the mesh nodes 1802a) of the DC map template 1700 are translated to the boundary of the patient-specific anatomical model (e.g., the adjusted SC model template 1500).

Figure 19:
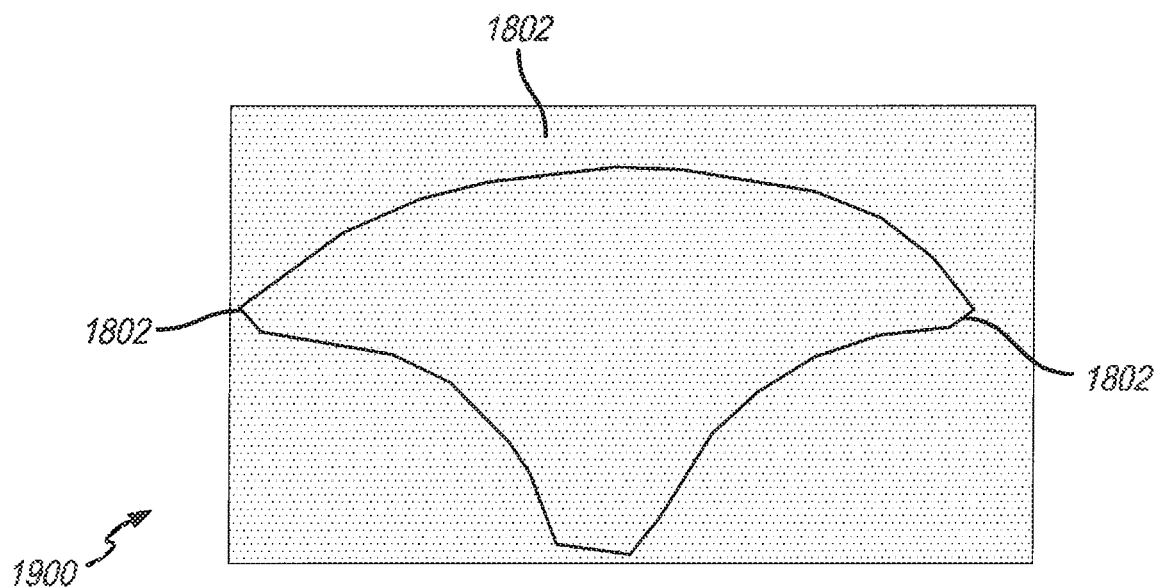
FIG. 19 is an illustration of a translated meshed DC map template, according to an embodiment of the present disclosure.

FIG. 19 illustrates a translated meshed DC map template 1900. The translated meshed DC map template 1900 may be formed using a triangulation technique algorithm (e.g., DeLaunay algorithm). For example, the system 100 may construct a background triangulation between an edge of the DC boundary 1704 of the DC map template 1700 and a set of sample points located on the DC map template 1700. The sample points may be received by the system 100 from the clinician or automatically selected based on contours of the DC map template 1700. The system 100 may further define descriptors of each mesh node 1802 with respect to the background triangulation, such as using barycentric coordinates within each triangle formed during the background triangulation.

Figure 20:
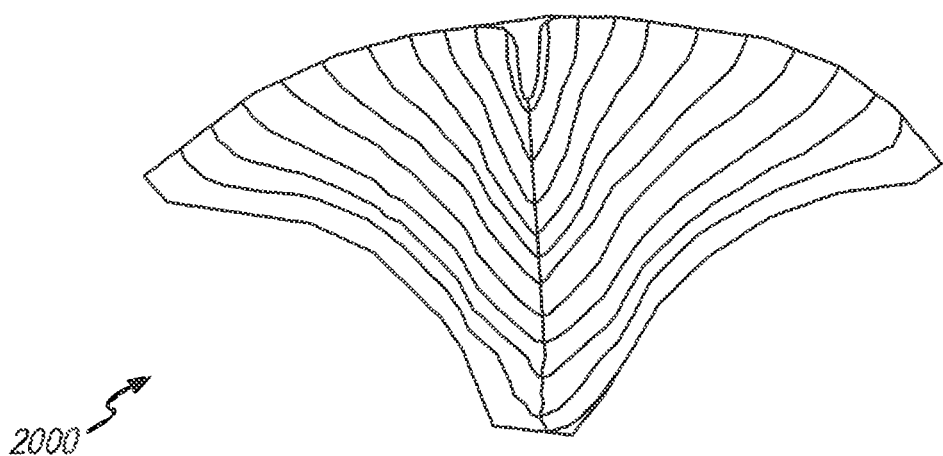
FIG. 20 is an illustration of a transformed DC map template, according to an embodiment of the present disclosure.

Once the descriptors are defined, the system 100 may adjust the background triangulation to incorporate the desired modification of the DC boundary 1704 to that of the DC boundary 1502 of the adjusted SC model template 1500 to form a transformed DC map template 2000 as shown in FIG. 20. Optionally, the system 100 may convert the descriptors of each mesh node 1802 to Cartesian coordinates based on the adjusted background triangulation. A technical effect of the translation operation is a transforming of the external DC boundary 1704 and the internal zone boundaries 1706 of the DC map template 1700.

Optionally, variations may be added during the translation operation at 1608 to account for uncertainties in dermatomal zone sizes and boundary locations. For example, artificial noise may be added during the movement such that a total distance moved by each mesh node 1802 may be adjusted by a small value using a random number generator centered on zero within the system 100. Additionally, or alternatively, variations may be added by adjusting the spacing of the mesh nodes 1802 or spacing of the sample points.

At 1610, the method 1600 calculates a shifted distance of the mesh nodes 1802. For example, the system 100 may calculate distance based on a position of one or more mesh nodes 1802 from before the translation operation at 1608 to a position of the one or more mesh nodes 1802 after the translation operation at 1608. Optionally, the method 1600 may include applying an image filter, such as an averaging image filter, based on a user-specified pixel size. The user specified pixel size may be received by the system 100 through the user interface. Additionally, or alternatively, the user specified pixel size may be predetermined and stored in memory (e.g., ROM 104, RAM 106, hard drive 108). The averaging image filter may be used to blend pixel locations of the transformed DC map template 2000.

Figure 21:
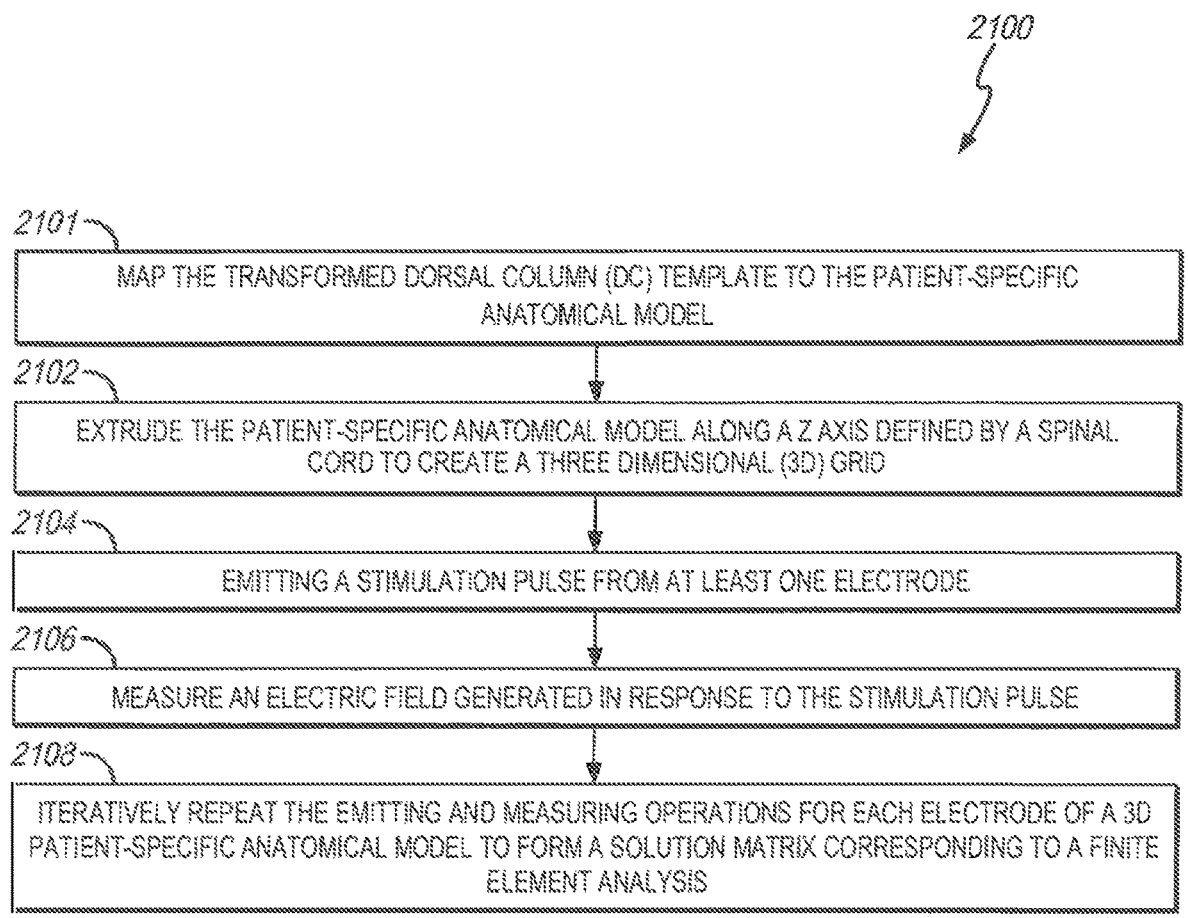
FIG. 21 is a flowchart of a method for mapping a patient-specific anatomical model to a transformed DC map template, in accordance to an embodiment of the present disclosure.

FIG. 21 is a flowchart of a method 2100 for mapping the patient-specific anatomical model to the transformed DC map template. The method 2100 may be employed by one or more of the components 52-58 described above, for example, the component 56. The method 2100 may employ structures or aspects of various embodiments (e.g., systems and/or methods) discussed herein. For example, a patient-specific anatomical model may be generated using the method 300 described above. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. Furthermore, it is noted that the following is just one possible method mapping the patient-specific anatomical model to the transformed DC map template. It should be noted, other methods may be used, in accordance with embodiments herein.

Beginning at 2101, the method 2100 maps the transformed DC map template 2000 to the patient-specific anatomical model. For example, the transformed DC map template 2000 and the adjusted SC model template 1500 may be one or more 2D geometries based on an X-Y plane (e.g., defined by the axes 703 and 701) based on a row of electrodes (e.g., 812) of the electrode array 511. The system 100 may define a coordinate origin (e.g., the coordinate origin 1403) aligned for both the transformed DC map template 2000 and the adjusted SC model template 1500 located at the distal end (e.g., the distal end 216) of the lead 402 at the Z axis (e.g., the axis 516), centered on the adjusted SC model template 1500 (e.g., for the x and y direction). Optionally, a file may be generated by the system 100 containing all of the dimensions of the electrodes 511 (e.g., size of the electrodes, spacing between electrodes, electrode layout design, and the like).

At 2102, the method 2100 extrudes the patient-specific anatomical model along the Z axis defined by the SC to create a three dimensional (3D) grid. The system 100 may extrude along the Z axis (e.g., the axis 516) defined by the SC along the lead 402 (or paddle structure 510) to create the 3D patient-specific anatomical structure. Optionally, the 3D patient-specific anatomical structure may be bounded by a 3D rectangular box to enclose the electrode array(s) 511 and SC tissue. The anatomical contours of the adjusted SC model template 1500 in the X-Y plane may be mapped into a 2D grid in the X-Y plane with pre-determined dx and dy increments. A material index (e.g. based on electrical conductivity) for the various SC tissues may be assigned by the system 100 for each grid point. The 2D grids with material index are duplicated along the Z axis to create a 3D grid within the rectangular box of the model. Optionally, the electrodes 511 and paddle structure 510 or lead 402 is mapped into the 3D grids with a corresponding material index.

At 2104, the method 2100 emitting a stimulation pulse from the at least one electrode (e.g., the electrode 511*a*). The stimulation pulse may be a simulated unit pulse (e.g., constant current or voltage) from at least one electrode within the 3D patient-specific anatomical model.

At 2106, the method 2100 measures an electric field generated in response to the stimulation pulse based on the 3D patient-specific anatomical model. For example, the electric field generated may be a simulated response based from a bidomain model (e.g., extracellular and intracellular domain) as corresponding to a position of the at least one electrode within the 3D patient-specific anatomical model.

At 2108, the method iteratively repeats the emitting and measuring operations at 2104 and 2106 for each electrode of the 3D patient-specific anatomical model to form a solution matrix corresponding to a bidomain model. The solution matrix may be formed by the system such that the matrix deposition/factoring would allow post processing for any combinations of stimulation contact configurations based on the superposition principle. For example, based on the superposition principle of the measured stimulation return signals for each individual electrodes 511 (e.g., 511*a*, 511*b*, 511*c*, 511*d*, 511*e*) within a selected combination is the sum of the stimulation return signals. A technical effect of the solution matrix is that the need to solve for each contact configuration tested is not needed, and therefore, greatly speeds up the calculation for the activated dermatomal zones.

Figure 22:
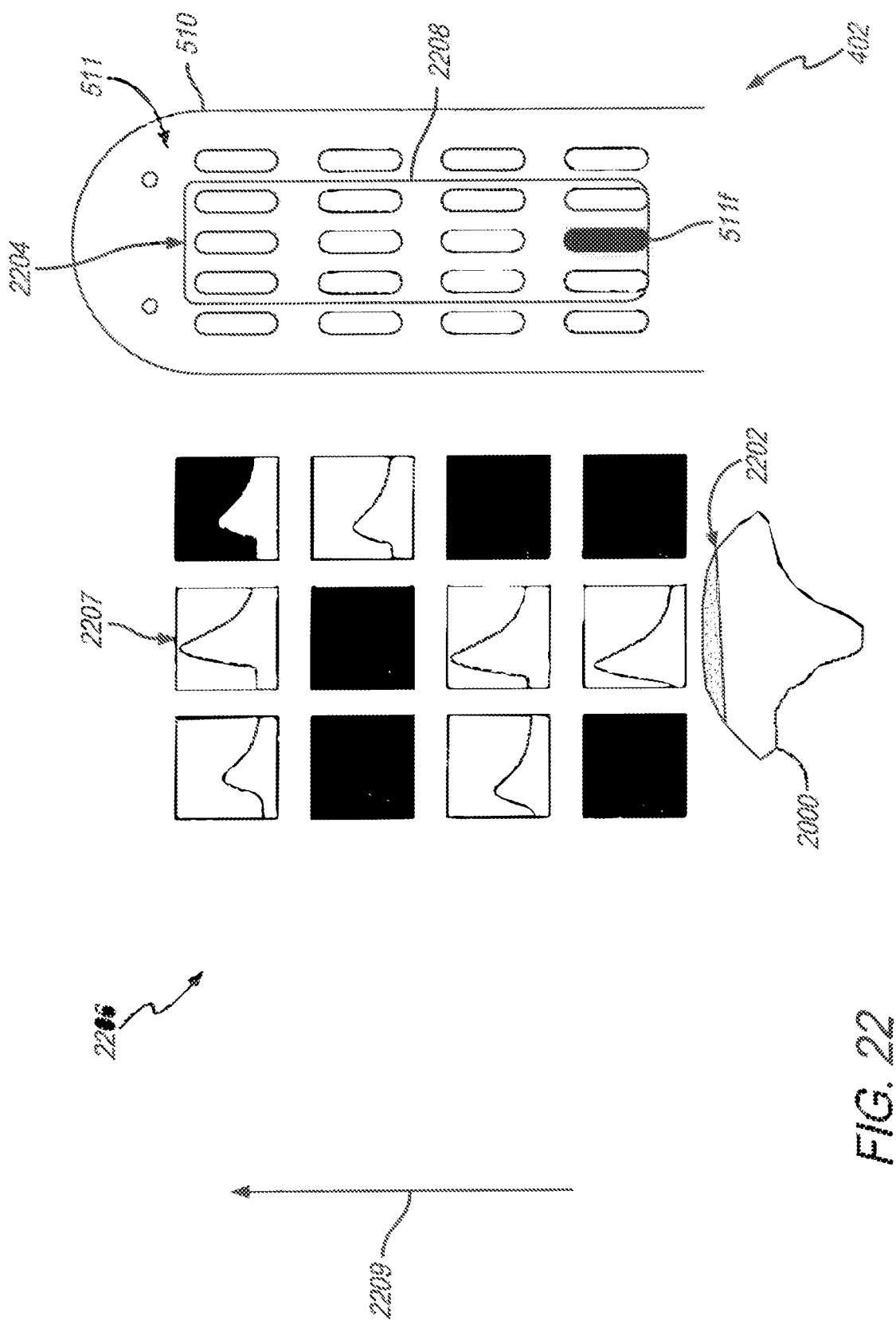
FIG. 22 is an illustration of stimulation return evoked compound action potential signals received by a lead, in accordance to an embodiment of the present disclosure.

Optionally, the method 2100 may include adjusting the patient-specific anatomical model based on the stimulation return signals (e.g., actual dermatomal zone activations) in response to emitted stimulation signals from at least one of the electrodes 2208. The stimulation return signal may include sensed ECAP signals 2206 made across a subset of electrodes 2208 (e.g., the electrodes 511 within the box) of the lead 402, and may be used to determine the activated dermatomal zones within the DC. FIG. 22 illustrates or example, when an SCS signal is emitted from the electrode 511f in a center column 2204, activation of fibers within the DC is expected near the DC midline 2202, and ECAP signals would propagate longitudinally (e.g., along a Z axis 2209) along the SC tissue. The propagation is reflected from the sensed ECAP 2206 of the central column 2207 corresponding to electrodes 511 above the emitting electrodes 511f along the Z axis 2209. By adjusting the amplitude of the SCS signal emitted from the electrode 511f, the first sensed ECAP signal (e.g., the stimulation return signal) at the lowest amplitude could be used as the estimated stimulation threshold. The sensed ECAP signals 2206 of the subset of electrodes 2208 may be used to refine the model location, such as adjusting the solution matrix, of activated dermatomal fiber tract zones for given stimulation configurations.

Additionally, or alternatively, a cross impedance may be determined by the system 100 and/or controller 251 based on the sensed ECAP signals 2206. For example, the cross impedance (variable $Z_c$) may be equal to the ECAP signal (variable $V_{sense}$) divided by stimulation current of the SCS signal (variable $I_{stim}$) as noted in Equation 3. This cross impedance may be used concurrently with the impedance signal measured at 306. Optionally the cross impedance may be used instead of the impedance signal measured at 306, for example, if the electrodes 511 have a high polarized impedance.

$$Z_c = V_{sense}/I_{stim} \tag{Equation 3}$$

The technical effect of the solution matrix used concurrently with the 3D patient-specific anatomical model forms the bidomain model. The bidomain model may be a finite element analysis (FEA) solution coupled with the biophysical cellular model of neural elements to determine the effect of SCS on the transmembrane potentials of nerve fibers in the SC. This allows the clinician to detect and locate sites of neural activation resulting from the SCS emitted from one or more of the electrodes 511. The biophysical cellular model may be a predetermined template included within the 3D patient-specific anatomical model used to define electrical and geometrical properties of a neuron for an applied stimulation from at least one of the electrodes 511. For example, the biophysical model may determine the response of a neuron based on an electrical characteristic of the applied stimulation pulse (e.g., amplitude, frequency, pulse width). The biophysical cellular model may include transmembrane ion channels, transmembrane capacitance, intracellular conductance, applied stimulation fields or the like.

Figure 23:
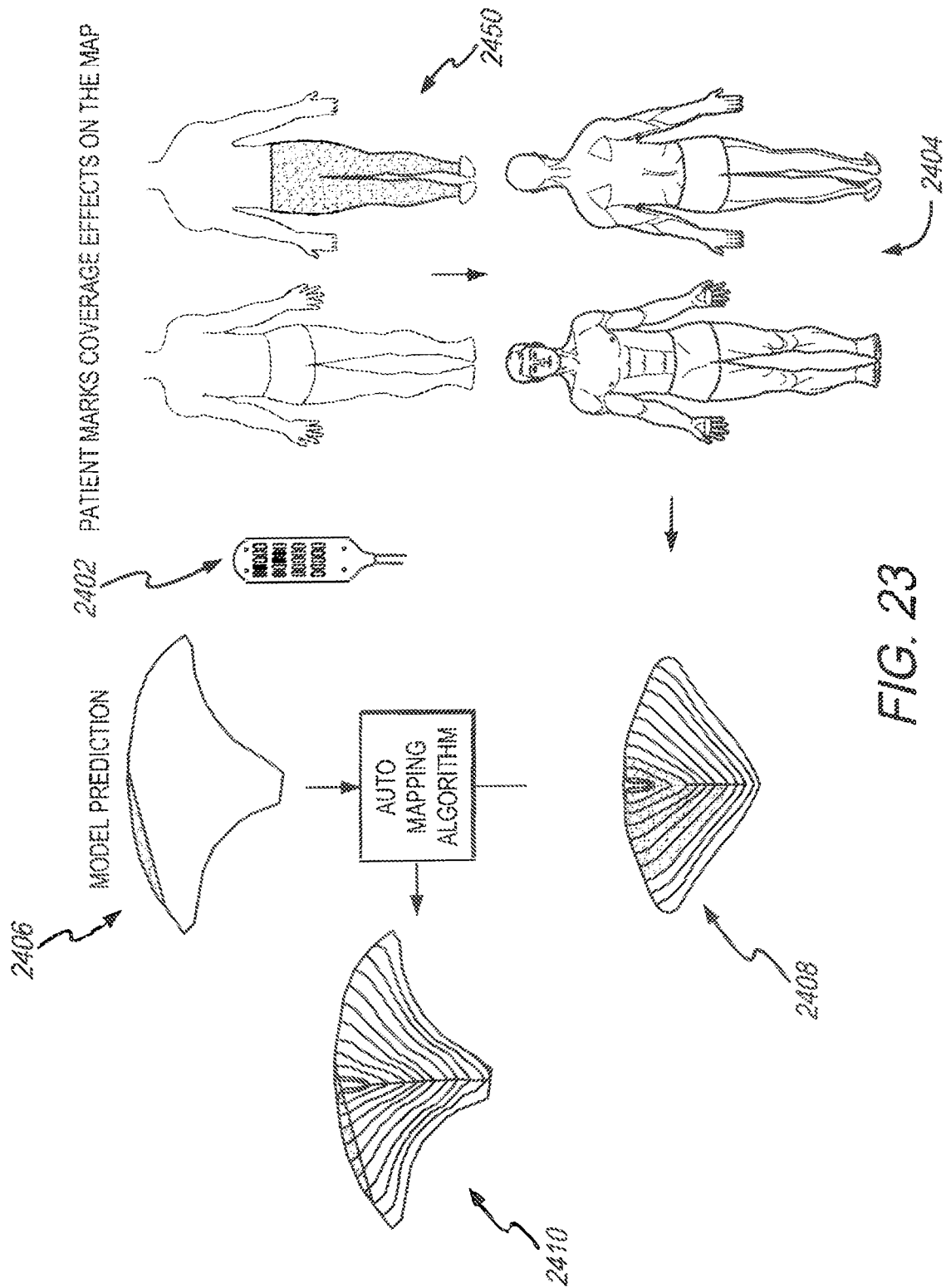
FIG. 23 is an illustration of a graphical user interface of a system, in accordance to an embodiment of the present disclosure.

In at least one embodiment, the graphical user interface of the system 100 may include graphical icons, scroll bars, buttons, and the like which may receive or detect user or touch inputs 134 for the system 100 when selections are made by the user. For example, the graphical user interface may allow the user to test the neural response to various pre-selected electrode configurations for input validation. FIG. 23 is an illustration of one possible graphical user interface (GUI) 2400 of the system 100. The GUI 2400 illustrates a pre-selected electrode configuration 2402 of the NS 200. The pre-selected electrode configuration 2402 may illustrate which electrodes are emitting SCS (e.g., in a cathode state, in an anode state). Additionally, or alternatively, the GUI 2400 may allow the clinician to test the pre-selected electrode configuration 2402 at several different patient postures, such as sitting, standing, supine, or the like. For example, patient stimulation responses at different patient postures provides input into a body dermatomal map 2404 on the display 122 corresponding to actual dermatomal zone activation in response to stimulations at the pre-selected electrode configuration 2402. A simulated DC activation region 2406 (e.g., based on the transformed DC map template 2000) is also displayed on the GUI 2400 based on the solution matrix of the 3D patient-specific anatomical model. The simulated DC activation region 2406 displays simulated dermatomal zones that are activated corresponding to the different patient postures at the pre-selected electrode configuration 2402. The actual and simulated activated dermatomal zones may automatically be compared by the CPU 102 with mapped zones 2408 of the DC based from patient responses at the different patient postures. By using activation regions from the simulation and dermatomal zones from the patient response, an automated algorithm stored in memory (e.g., ROM 104, RAM 106, hard drive 108) and executed by the CPU 102 to refine or adjust the 3D patient-specific anatomical model parameters, including dermatomal zone locations 2410 of the DC.

Figure 24:
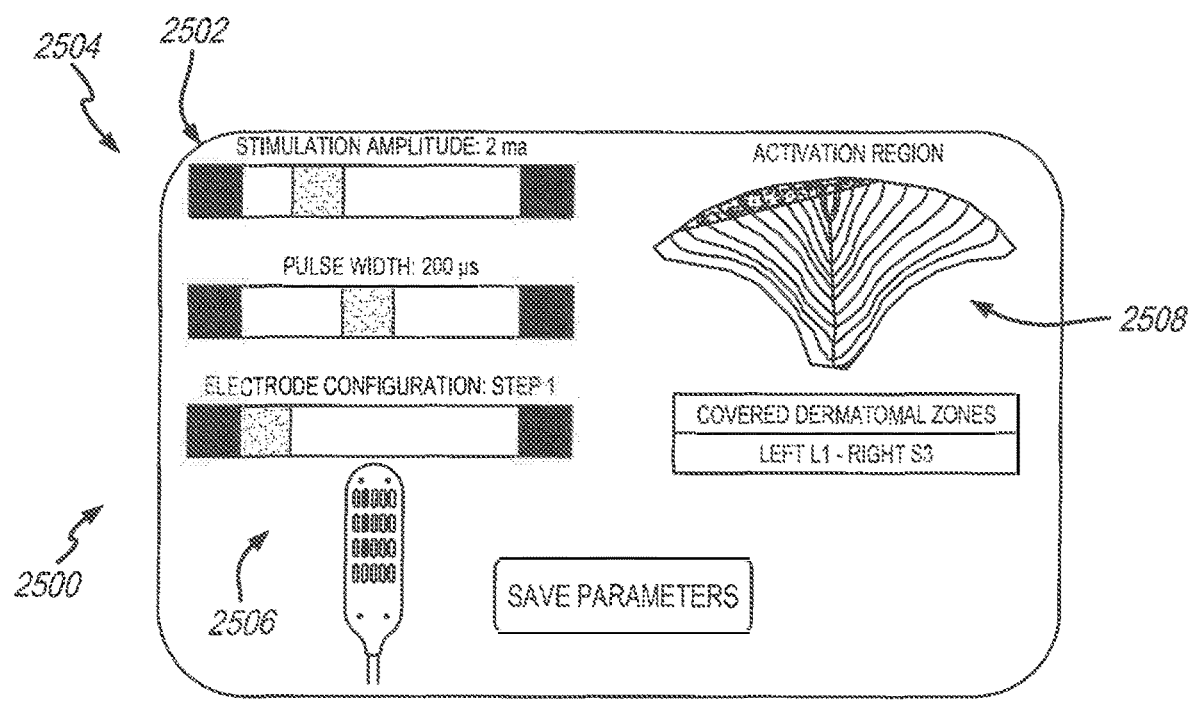
FIG. 24 is an illustration of a graphical user interface of a system, in accordance to an embodiment of the present disclosure.

Optionally, the GUI 2400 may include use of a predetermined or user-defined trolling algorithm that steps through a selected set of electrode configurations. In at least one embodiment a GUI 2500, as shown in FIG. 24, may allow the clinician to define model parameters such as stimulation amplitude 2502, pulse width 2504, and/or to select electrode configuration(s) 2506 from an existing library (e.g., stored in the ROM 104, RAM 106, or hard drive 108) or to define a custom set of configurations. The selected configurations 2506 may be simulated from the mapped patient-specific model (e.g., from the method 2100) and the results may be displayed as an illustration of activated dermatomal zone locations 2508 on the display 122.

Figure 25:
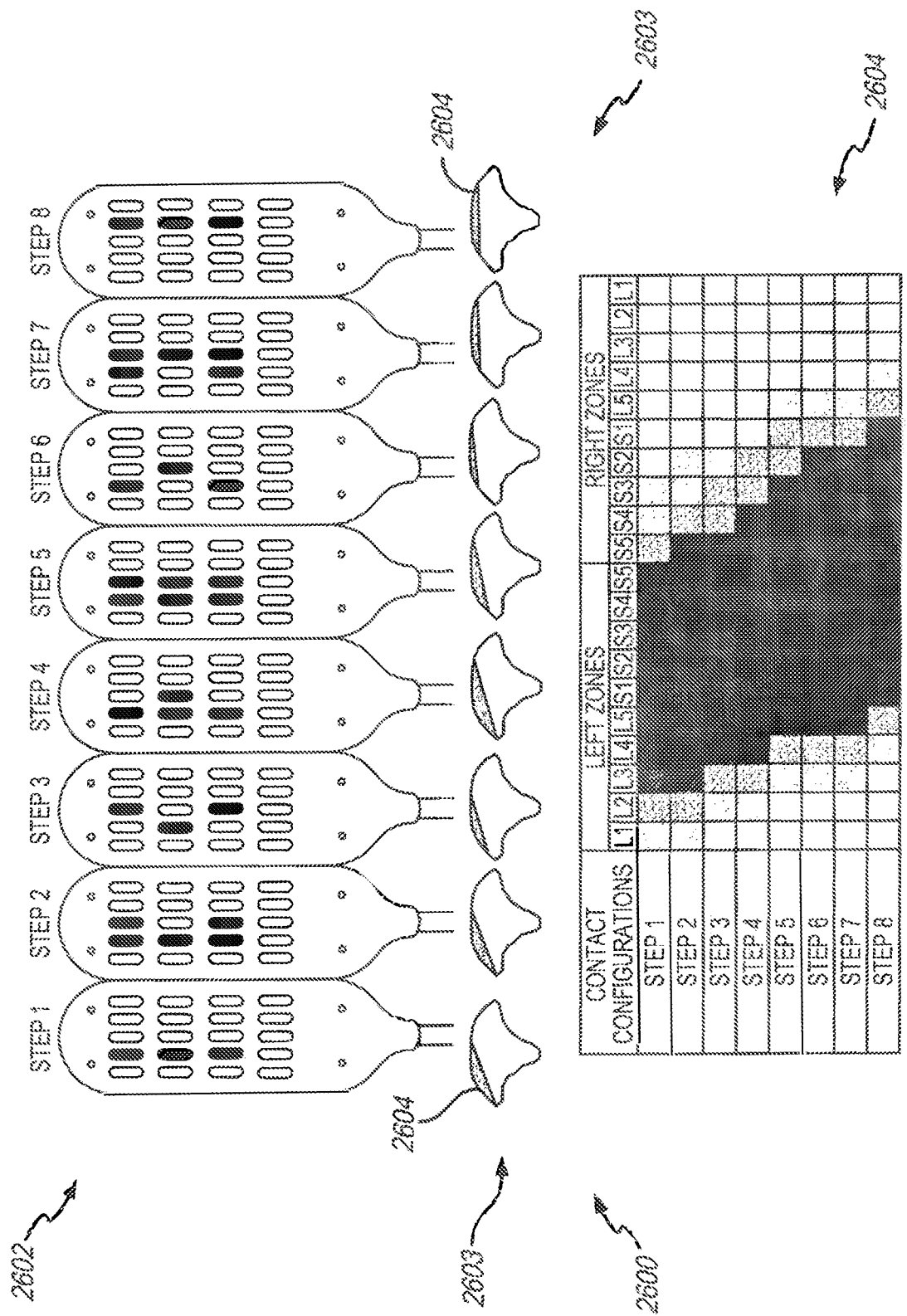
FIG. 25 is an illustration of a graphical user interface of a system, in accordance to an embodiment of the present disclosure.

Additionally, or alternatively, a GUI 2600 of the system 100, as shown in FIG. 25, may display an illustration with the solved activation areas 2604 and mapped dermatomal zones 2603 corresponding to an electrode configuration 2602. The GUI 2600 may be used to test different SCS settings that best target specific painful dermatomes, or to automatically determine the optimal settings using an automated optimization routine. Further, the mapped dermatomal zones 2603 display the amount (e.g., area in each zone, number of fibers in each zone) of dermatomal zones activated for each electrode configuration 2602 illustrated as activation area 2604.

Figure 26:
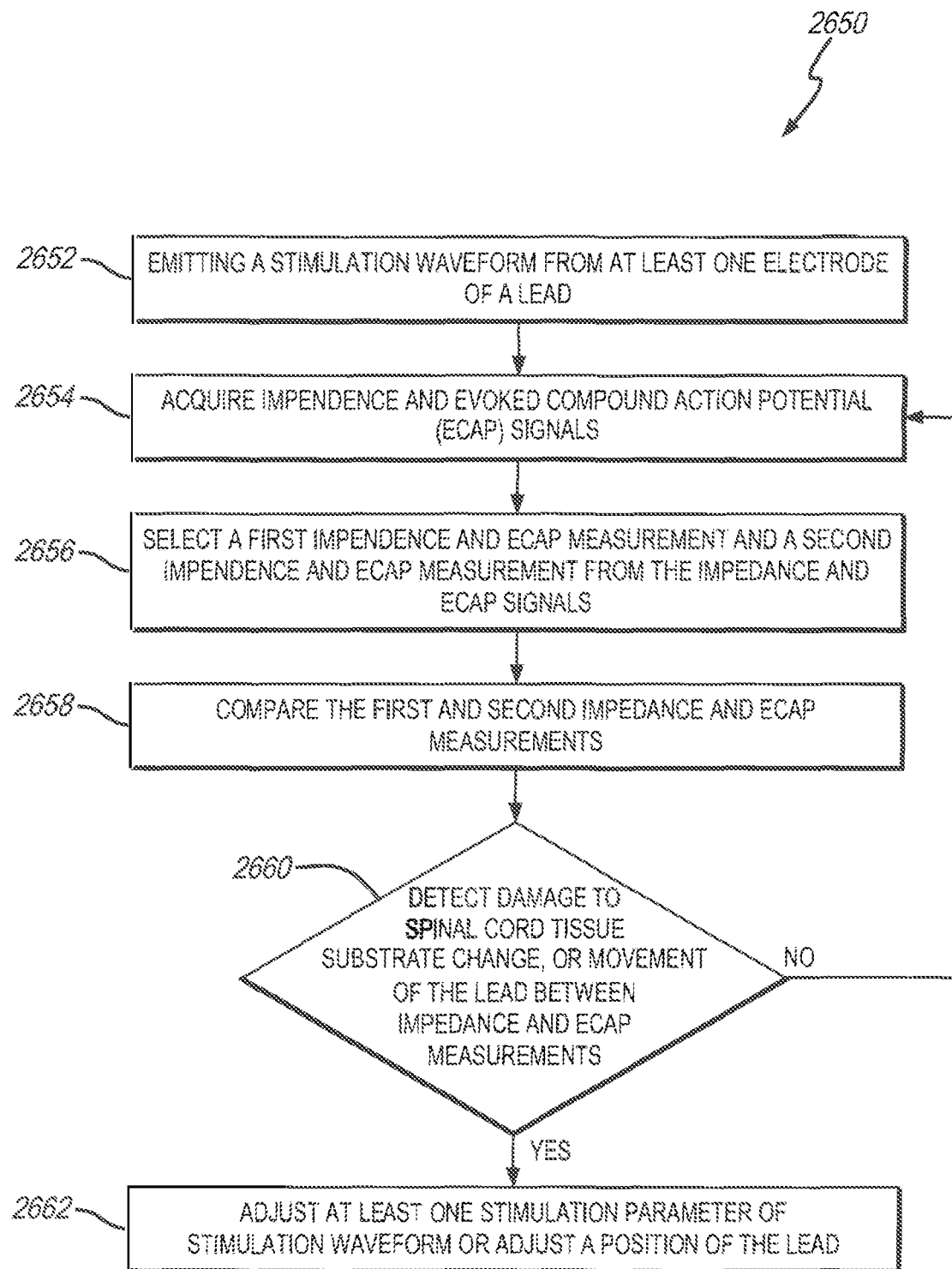
FIG. 26 is a flowchart of a method for differentiating between spinal cord tissue damage and changes in electrode position based on impedance and evoked compound action potential measurements, in accordance to an embodiment of the present disclosure.

Additionally, or alternatively, in connection with a method 2650 shown in FIG. 26, the impedance signal acquired at 306 (shown in FIG. 3) and the ECAP signal acquired at 308 may be used by the controller 251 to differentiate between a change in position or movement of the lead 402 (shown in FIG. 4) and neural tissue damage of the SC or substrate changes proximate to the lead 402.

Neural tissue damage may occur during implantation of the lead 402 into the patient, or stimulation of the neurons of the stimulation target in response to the drive signal, and/or the like. For example, pressure applied to the SC by the lead 402 during implantation damages the corresponding neural tissue. Alternatively, stimulation may cause neuronal tissue damage through over-activation of neurons or generation of potentially harmful electrochemical reactions. Damaged neurons may not generate an ECAP in response to the drive signal, and thereby not contributing to the ECAP signal reducing the magnitude of the ECAP signal (e.g., the peak to peak magnitude 1320 of FIG. 13) relative to non-damaged neurons in response to the drive signal.

Substrate changes correspond to changes in a composition of tissue surrounding the CSF (e.g., the CSF 508 of FIG. 5) and lead 402. For example, the immune system of the patient may respond and/or react to the presence of the lead 402 within the epidural space 404 or a disease progression within the SC tissue by generating connective tissue around the lead 402 and/or the electrodes 511. The connective tissue may encapsulate and/or surround portions of the lead 402, displacing or compressing the CSF 508. The connective tissue may reduce the conductivity of the tissue between the electrodes 511 and the stimulation target affecting the impedance signal measured by the IPG 412.

FIG. 26 illustrates a flowchart of the method 2650 to differentiate between neural damage of the SC, substrate change, and lead or electrode position changes based on the impedance and ECAP measurements. The method 2650 may employ structures or aspects of various embodiments (e.g., systems and/or methods) discussed herein. Optionally, the operations of the method 2650 may represent actions to be performed by one or more circuits (e.g., the controller 251) that include or are connected with processors, microprocessors, controllers, microcontrollers, Application Specific Integrated Circuits (ASICs), Field-Programmable Gate Arrays (FPGAs), or other logic-based devices that operate using instructions stored in a tangible and non-transitory computer readable medium (e.g., a computer hard drive, ROM, RAM, EEPROM, flash drive, or the like), such as software, and/or that operate based on instructions that are hardwired into the logic of the. For example, the operations of the method 2650 may represent actions of or performed by one or more processors when executing programmed instructions stored in a tangible and non-transitory computer readable medium.

In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. It should be noted, other methods may be used, in accordance with embodiments herein.

One or more methods may (i) emit a stimulation waveform from at least one electrode of a lead, (ii) acquire impedance and evoked compound action potential (ECAP) signals, (iii) select a first impedance and ECAP measurement and a second impedance and ECAP measurements from the impedance and ECAP signals, (iv) detect spinal cord (SC) tissue damage based on a difference between the second ECAP measurement and the first ECAP measurement, and (v) adjust at least one stimulation parameter to change the stimulation waveform or adjust the location of the lead 402 based on detection of the SC tissue damage.

Beginning at 2652, the lead 402 (shown in FIG. 4) emits a stimulation waveform from at least one electrode 511 (shown in FIG. 5). The stimulation waveform may be similar to and/or the same as the drive signal at 304. For example, the stimulation waveform may be generated from the IPG 412, such as from generating circuitry (e.g., the generating circuitry 252 of FIG. 2), and conducted to at least one of the electrodes 511 via switching circuitry (e.g., the switching circuitry 257) and the lead 402. The stimulation waveform may represent a current pulse (e.g., a monophasic pulse) or a series of current pulses (e.g., a biphasic pulse, tri-phasic pulses), a sinusoidal waveform, a burst waveform, and/or the like which are emitted from at least one of the electrodes 511 with a predetermined amplitude and pulse width. Additionally, or alternatively the stimulation waveform may be a voltage pulse with a predetermined amplitude and pulse width. Optionally, the stimulation waveform may be repeatedly emitted by the electrodes 511 based on an SCS program.

At 2654, the lead acquires impedance and ECAP signals. The impedance and ECAP signals are generated in response to the stimulation waveform. As further described in connection to 306 of FIG. 3, the impedance signal may be a discrete impedance value measured periodically by the controller 251 or a calculated impedance measured continuously over time during the stimulation waveform.

Figure 27:
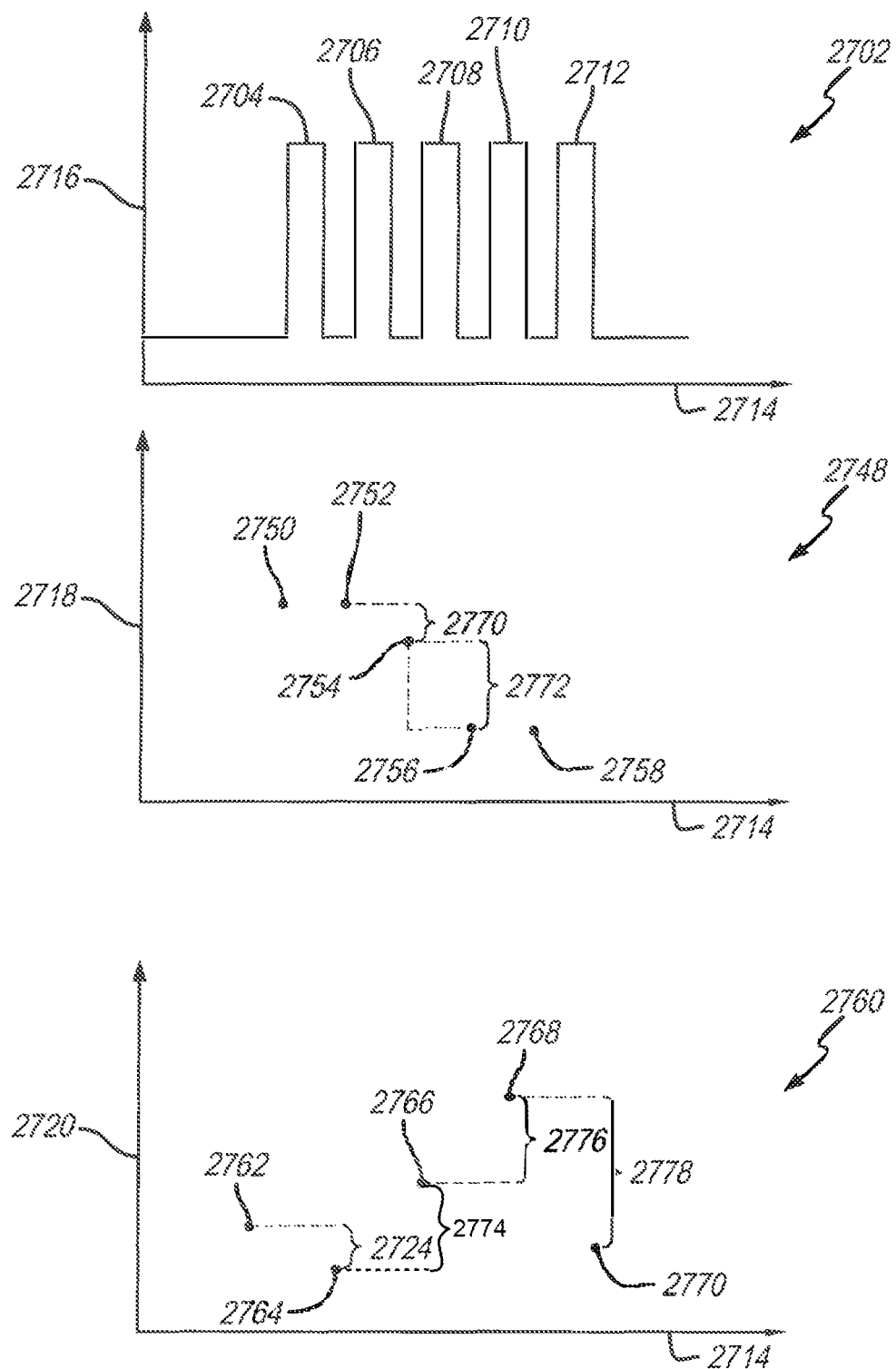
FIG. 27 is a graphical illustration of a stimulation waveform with corresponding impedance and evoked compound action potential measurements magnitudes, in accordance to an embodiment of the present disclosure.

FIG. 27 is a graphical illustration of a stimulation waveform 2702 with a corresponding impedance signal 2748 and ECAP measurements 2760. The stimulation waveform 2702, the impedance signal 2748, and the ECAP measurements 2760 are plotted along a horizontal axis 2714 representing time.

The stimulation waveform 2702 may be emitted from one or more electrodes 511 as shown in FIG. 5. The stimulation waveform 2702 may be formed by a series of pulses 2704-2712 emitted over time represented along the horizontal axis 2714 with an EP magnitude (e.g., current, voltage) represented by the vertical axis 2716. Parameters for the pulses 2704-2712 such as pulse width, amplitude, frequency, and/or the like may be based on the SCS program.

The impedance signal 2748 is formed by impedance measurements 2750-2758 plotted with respect to a vertical axis 2718 representing a magnitude (e.g., ohms) acquired during the pulses 2704-2712 of the stimulation waveform 2702. Additionally, or alternatively, in other embodiments the impedance signal 2748 may be measured continuously by the sensing circuitry 258 and/or controller 251.

The impedance signal 2748 may be acquired similar to and/or the same as the impedance signal acquired at 306 of FIG. 3. For example, the pulses 2704-2712 forming the stimulation waveform 2702 may be emitted by the electrodes 511$d$ (e.g., in an anode state) and 511$h$ (e.g., in a cathode state). An electric potential or voltage may be measured across the electrodes 511$d$ and 511$h$ by the sensing circuitry 258 and/or the controller 251. For example, the sensing circuitry 258 may compare the voltage potentials at the electrodes 511$d$ and 511$h$ during each of the pulses 2704-2712. Using Equation 1, the controller 251 may determine impedance measurements 2750-2758 forming the impedance signal 2748 by dividing the measured voltage during each pulse 2704-2712 by the corresponding amplitude of the pulses 2704-2712.

The ECAP measurements 2760 may correspond to a plurality of peak to peak measurements 2762-2770 plotted with respect to a vertical axis 2720 representing magnitude. The ECAP measurements 2760 may be derived from ECAP signals measured at one or more of the electrodes 511 during the stimulation waveform 2702 and received by the sensing circuitry 258.

For example, the electrode 511$h$ may measure the EP during each of the pulses 2704-2712. The EP may be generated from neurons of the stimulation target in response to the pulses 2704-2712 emitted by one or more electrodes 511. The measured EP measurements form an ECAP signal for each pulse 2704-2712, such as the ECAP signal 1302 and/or 1303 shown in FIG. 13. The system 100 and/or the controller 251 may determine when the maximum peak (e.g., 1317, 1319) and minimum peak (e.g., 1316, 1318) occurs based on changes in the slope of the ECAP signal. For example, the controller 251 may determine when the maximum peak 1317 occurs based on when the slope changes magnitude from positive to negative. In another example, the controller 251 may determine when the minimum peak 1316 occurs when the slope changes from negative to positive.

The controller 251 may determine the peak to peak measurements 2762-2770 based on a difference in magnitude (e.g., EP) between the maximum peak (e.g., 1317, 1319) and the minimum peak (e.g., 1316, 1318) for each ECAP signal corresponding to the pulses 2704-2714.

Returning to FIG. 26, the controller 251 at 2658 selects a first impedance and ECAP measurement and a second impedance and ECAP measurement from the impedance and ECAP signals. The second impedance and ECAP measurement may be temporally separated from the first impedance and ECAP measurement.

For example, the selected impedance and ECAP measurements may correspond to two different pulses within the stimulation waveform 2702. The controller 251 may select the impedance measurement 2752 and the peak to peak ECAP measurement 2764 corresponding to the pulse 2706 as the first impedance and ECAP measurement, and the impedance measurement 2754 and the peak to peak measurement 2766 as the second impedance and ECAP measurement. It should be noted in other embodiments the ECAP measurements may correspond to amplitudes of the maximum peak (e.g., 1317, 1319), amplitudes of the minimum peak (e.g., 1316, 1318), and/or the like of the ECAP signal.

At 2660, the controller 251 may detect damage to neural tissue of SC, a substrate change, or movement of the lead 402 (FIG. 4). In connection with FIGS. 28 and 29, the controller 251 may detect and/or determine when damage to the SC tissue, the substrate change, and/or movement of the lead 402 based on a difference between the second impedance and/or ECAP measurement and the first impedance and/or ECAP measurement.

FIG. 28 illustrates a decision table 2800 utilized by the controller 251 for detecting SC tissue damage, substrate change, and/or movement of a lead. The decision table 2800 includes an impedance column 2802 and an ECAP amplitude column 2804 with a corresponding determination listed in the column 2806. The controller 251 may determine SC tissue (e.g., neural tissue) damage, substrate change, and/or movement of the lead 402 based on a relationship between the first impedance and ECAP measurement and the second impedance and ECAP measurement. For example, the controller 251 may detect SC tissue damage based on a predetermined combination of i) an ECAP difference between first and second ECAP measurements and ii) an impedance difference between first and second impedance measurements.

The impedance column 2802 corresponds to differences determined by the controller 251 between the first impedance measurement (e.g., the impedance measurement 2752) and the second impedance measurement (e.g., the impedance measurement 2754) selected at 2658 of FIG. 26.

For example, the controller 251 may determine whether the impedance increases, decreases, and/or does not change from the first impedance measurement to the second impedance measurement based on a predetermined impedance threshold. The predetermined impedance threshold may be stored in the memory 261, and correspond to a minimum amount of change between the two selected impedance measurements that will be determined and/or verified by the controller 251 as an increase and/or decrease in impedance.

For example, the predetermined impedance threshold may correspond to an amount of change between the impedance measurements that is greater than electrical noise (e.g., additive noise, electromagnetic interference, signal-to-noise ratio) generated by the operation of the IPG 250. The predetermined impedance threshold may be a percentage corresponding to an amount of change between the second and the first impedance measurement (e.g., three percent change, five percent change). In another example, the predetermined impedance threshold may correspond to a rate of change (e.g., slope, differential) determined from the first and second impedance measurements. The controller 251 may compare a difference or delta between the second impedance measurement (e.g., the impedance measurement 2754) and the first impedance measurement (e.g., the impedance measurement 2752) with the predetermined impedance threshold to determine whether the impedance has changed (e.g. increased, decreased) from the first impedance measurement to the second impedance measurement.

For example, the controller 251 may select the impedance measurement 2752 and the impedance measurement 2754. The controller 251 may calculate a difference 2770 of, for example a two percent drop, between the impedance measurements 2752-2754. The controller 251 may compare the difference 2770 with the predetermined impedance threshold of, for example three percent. It should be noted that in other embodiments the predetermined impedance threshold may be greater than or less than three percent. If the magnitude of the difference 2770 is greater than the threshold, the controller 251 may determine that the impedance changed (e.g., increased, decreased) between the first and second impedance measurements. Alternatively, if the magnitude of the difference 2770 is lower than the threshold, the controller 251 may determine that the impedance did not change. For example, the controller 251 may determine that since the difference 2770 (e.g., a two prevent) is below the predetermined impedance threshold (e.g., three percent) the impedance measurements did not change.

Based on a determination that the impedance has not changed between impedance measurements, the controller 251 may determine that the substrate surrounding the lead 402 has not changed. For example, as indicated along row 2808 in the decision table 2800, a substrate change is shown based on a change in impedance. Since the controller 251 determined that the impedance measurements did not change, the controller 251 may determine that a substrate change surrounding the lead 402 has not occurred.

The ECAP amplitude column 2804 corresponds to differences determined by the controller 251 between the first ECAP measurement (e.g., the peak to peak measurement 2764) and the second ECAP measurement (e.g., the peak to peak measurement 2766) selected at 2658 of FIG. 26.

For example, the controller 251 may determine whether the ECAP measurement increases, decreases, and/or does not change from the first ECAP measurement to the second ECAP measurement based on a predetermined ECAP amplitude threshold. The predetermined ECAP amplitude threshold may be stored in the memory 261, and correspond to an amount of change between two ECAP measurements that can be determined and/or verified by the controller 251 as an increase and/or decrease in ECAP amplitude.

For example, the predetermined ECAP amplitude threshold may correspond to an amount of change between the ECAP measurements that is greater than electrical noise (e.g., additive noise, electromagnetic interference, signal-to-noise ratio) generated by the operation of the IPG 250. The predetermined ECAP amplitude threshold may be a percentage corresponding to an amount of change between the second and the first ECAP measurements (e.g., three percent change, five percent change). In another example, the predetermined ECAP amplitude threshold may correspond to a rate of change (e.g., slope, differential) determined from the first and the second ECAP measurements. The controller 251 may compare a difference or delta between the second ECAP (e.g., the peak to peak measurement 2766) and the first ECAP measurement (e.g., the peak to peak measurement 2764) with the predetermined ECAP amplitude threshold to determine whether the ECAP amplitude has changed from the first ECAP measurement to the second ECAP measurement.

For example, the controller 251 may select the peak to peak measurement 2764 and the peak to peak measurement 2766. The controller 251 may calculate a difference 2774 (e.g., at 2658 of FIG. 26), for example a one and a half percent increase, between the ECAP measurements 2764-2766. The controller 251 may compare the difference 2774 with the predetermined ECAP amplitude threshold of, for example of three percent. It should be noted that in other embodiments the predetermined ECAP amplitude threshold may be greater than or less than three percent. If the magnitude of the difference 2774 is greater than the threshold, the controller 251 may determine that the ECAP amplitude changed between the ECAP measurements. Alternatively, if the magnitude of the difference 2774 is lower than the threshold, the controller 251 may determine that the ECAP amplitude did not change. For example, the controller 251 may determine that since the difference 2774 (e.g., a one and a half percent increase) is below the predetermined ECAP amplitude threshold (e.g., three percent) the ECAP measurements did not change.

Based on a determination that the ECAP amplitudes have not changed between ECAP measurements, the controller 251 may determine that the lead 402 has not moved relative to the SC tissue between the ECAP measurements and the SC tissue is not damaged. For example, as indicated along rows 2810, 2812, 2814, 2816, 2820, and 2821 in the decision table 2800, a movement in the lead 402 and damage to the SC tissue is shown based on a change in ECAP amplitude. Since the controller 251 determined that the ECAP measurements did not change, the controller 251 may determine that the lead 402 did not move between the ECAP measurements and/or the SC tissue is not damaged.

In various embodiments, the controller 251 may compare the ECAP measurements to a critical threshold. The critical threshold may be stored in the memory 261. The critical threshold may correspond to a change between the two ECAP measurements indicating neural tissue damage of the SC. The critical threshold is greater than the ECAP amplitude threshold. For example, the critical threshold may be a percentage corresponding to an amount of change between the first and the second ECAP measurement (e.g., thirty percent change, forty percent change, fifty percent change). In another example, the predetermined EACP amplitude threshold may correspond to a rate of change (e.g., slope, differential) determined from the first and second ECAP measurement.

Figure 29:
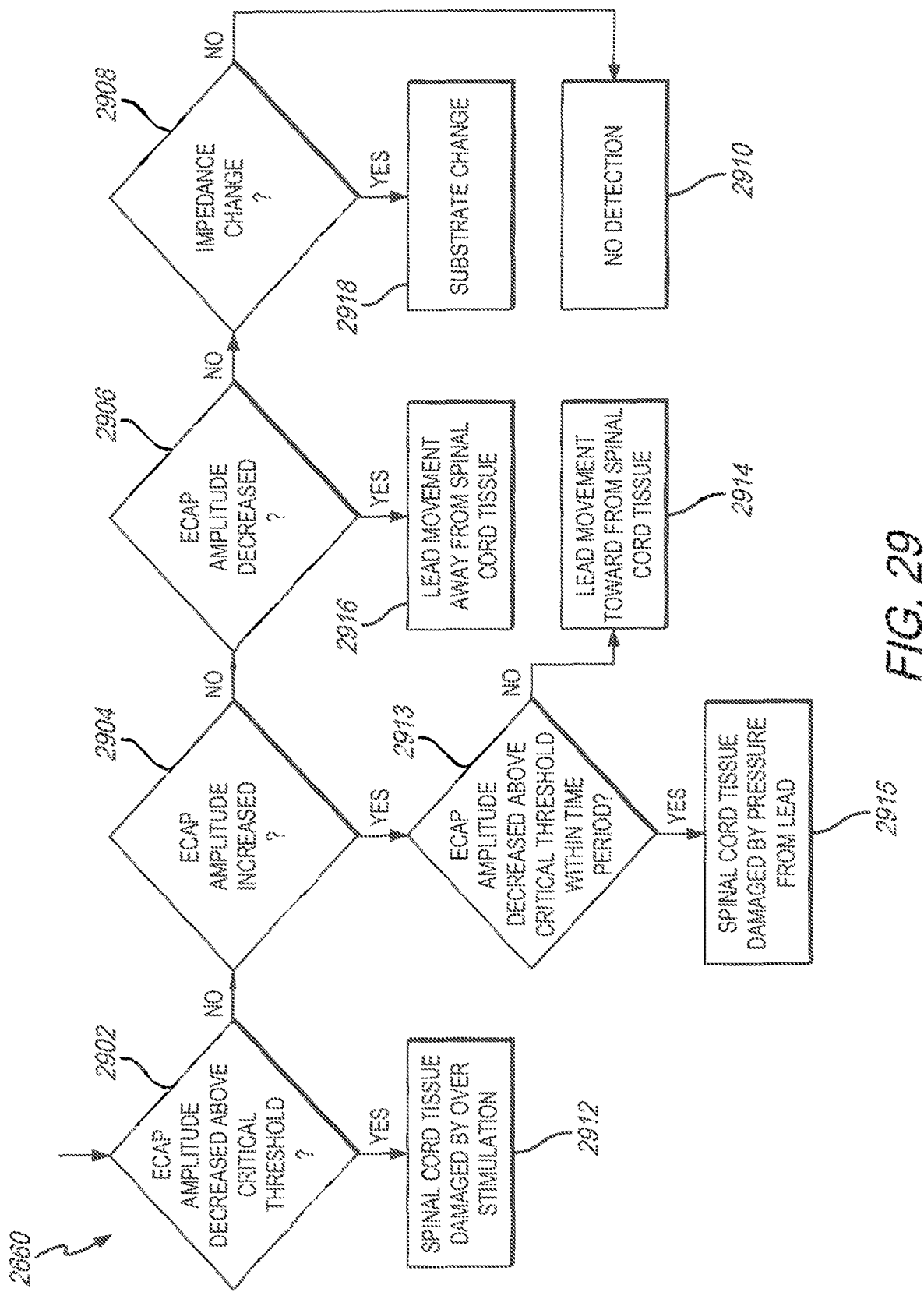
FIG. 29 is a flowchart for detecting spinal cord tissue damage, substrate change, and/or movement of a lead, in accordance to an embodiment of the present disclosure.

FIG. 29 illustrates a flow chart of a method of a plurality of operations performed by the controller 251 at 2660 (FIG. 26) to detect damage to neural tissue of the SC, substrate change, and/or movement of the lead 402 described at 2660 of FIG. 26. The method is based on the decision table 2800.

Beginning at 2902, the controller 251 determines whether the ECAP amplitude has decreased between the first ECAP measurement and the second ECAP measurement more than the critical threshold. For example, the controller 251 may select at 2656 (FIG. 26) the peak to peak measurement 2766 as the first ECAP measurement and the peak to peak measurement 2768 as the second ECAP measurement. It should be noted that the peak to peak measurements 2766-2768 are temporally separated from each other, resulting from different pulses 2706-2708, respectively, of the stimulation waveform 2702. At 2658 (FIG. 26), the controller 251 may compare the peak to peak measurements 2762-2764 to determine a difference 2724, for example a ten percent decrease, between the ECAP measurements. For example, the peak to peak measurement 2764 is ten percent lower than the peak to peak measurement 2762. The controller 251 may compare the difference 2724 with the predetermined critical threshold, for example of thirty percent. Since, the difference 2724 is lower than the critical threshold, the controller 251 may determine that no neural tissue damage of the SC due to over stimulation is detected.

Alternatively, if the magnitude of the difference 2724 was greater than the critical threshold, the controller 251 may determine, at 2912, neural tissue damage of the SC at and/or proximate to the stimulation target due to overstimulation.

At 2904, the controller 251 determines whether the ECAP amplitude has increased between the first ECAP measurement and the second ECAP measurement. The controller 251 may compare the difference 2776 determined at 2658 with the predetermined ECAP amplitude threshold to determine whether an increase of the ECAP measurement corresponds to lead 402 movement. For example, the difference 2776 corresponds to an increase in the second ECAP measurement (e.g., the peak to peak measurement 2768) of twenty percent. The controller 251 may compare the difference 2776 with the predetermined ECAP amplitude threshold of, for example, three percent. Since the difference 2776 is greater than the predetermined ECAP amplitude threshold, the controller 251 may determine that the ECAP amplitude increased.

Alternatively, if the difference 2776 is lower than the predetermined ECAP amplitude threshold, the controller 251 may determine that the ECAP amplitude did not increase and that the lead 402 did not move towards the SC tissue and/or stimulation target.

At 2913, the controller 251 determines whether the ECAP amplitude decreased above the critical threshold within a time period. The time period may be based on a number of subsequent pulses of the stimulation waveform 2702, relative to the peak to peak measurement used in 2904. For example, the time period may correspond to when the successive pulse 2712 occurs relative to the pulse 2710 which corresponds to the peak to peak measurement 2768. Additionally, or alternatively, the time period may be based on a number of a subsequent stimulation waveforms, relative to the peak to peak measurement used in 2904. In various embodiments, the time period may be based on time length, such as seconds, minutes, and/or hours.

Optionally, a length of the time period may be based on a procedure being performed on the patient. For example, during implantation of the lead 210 into the patient, the controller 251 may have the time period be a short period (e.g., several seconds, less than minutes). When the implantation is complete, the controller 251 may have the time period be longer relative to the implantation procedure (e.g., several hours, days).

After the time period, the controller 251 may determines whether the ECAP amplitude has decreased between the ECAP measurement used in 2904, the peak to peak measurement 2768, and a second ECAP measurement after the time period. For example, the time period may be based on the subsequent pulse, the pulse 2712. The controller 251 may select the corresponding peak to peak measurement 2770 as the second ECAP measurement. The controller 251 may compare the peak to peak measurements 2768-2770 to determine a difference 2778, for example a thirty-five percent decrease, between the ECAP measurements (e.g., 2768-2770). For example, the peak to peak measurement 2770 is thirty-five percent lower than the peak to peak measurement

2768. The controller 251 may compare the difference 2778 with the predetermined critical threshold, for example of thirty percent. Since, the difference 2778 is lower than the critical threshold, the controller 251 may determine, at 2915, that neural tissue damage of the SC due to pressure from the lead 402 is detected.

Alternatively, if the controller 251 determines at 2913 that the ECAP amplitude did not decrease above the critical threshold after the time period, then at 2914, the controller 251 may determine that the ECAP amplitude increase at 2904 is due to lead 402 movement toward the SC tissue.

At 2906, the controller 251 determines whether the ECAP amplitude has decreased. The controller 251 may compare a difference between the first ECAP measurement and the second ECAP measurement determined at 2658 with the predetermined ECAP amplitude threshold to determine whether a decrease from the first ECAP measurement to the second ECAP measurement corresponds to lead 402 moving away from the SC and/or stimulation. If the difference is greater than the predetermined ECAP amplitude threshold, the controller 251 at 2916 may determine that the ECAP amplitude decrease is due to lead 402 movement away from the SC tissue and/or stimulation target. Alternatively, if the difference is lower than the predetermined ECAP amplitude threshold, the controller 251 may determine that the lead 402 did not move away from the SC tissue and/or stimulation target.

At 2908, the controller 251 determines whether the impedance has changed (e.g., increased, decreased) between the first impedance measurement and the second impedance measurement above the predetermined impedance threshold. For example, the controller 251 may select at 2656 (FIG. 26) the impedance measurement 2754 as the first impedance measurement and the impedance measurement 2756 as the second impedance measurement. It should be noted that the impedance measurements 2754-2756 are temporally separated from each other, resulting from different pulses 2706-2708, respectively, of the stimulation waveform 2702. At 2658 (FIG. 26), the controller 251 may compare the impedance measurements 2754-2756 to determine a difference 2772, for example a fifteen percent decrease, between the impedance measurements 2754-2756. For example, the impedance measurement 2756 is fifteen percent lower than the impedance measurement 2754. The controller 251 may compare the difference 2772 with the predetermined impedance threshold of, for example of five percent. If the magnitude of the difference 2772 is higher than the predetermined impedance threshold, at 2918, the controller 251 may determine a substrate change proximate to the lead 402. If the magnitude of the difference 2772 is below and/or lower than the predetermined impedance threshold, the controller 251 may determine, at 2910, that no neural tissue damage, lead 402 movement, or substrate change is detected.

Returning to FIG. 26, if the controller 251 detects damage to the SC tissue, a substrate change, or movement of the lead, at 2662, the controller 251 may adjust at least one stimulation parameter of the stimulation waveform 2702 or may indicate a need to re-position the lead 402. The stimulation parameter of the stimulation waveform 2702 may correspond to an amplitude, frequency, number of pulses, and/or the like of the stimulation waveform 2702. One or more of the stimulation parameters may be adjusted by the controller 251 based on the detection (e.g., damage of the SC tissue 2912, lead 402 movement towards the SC tissue 2914, lead 402 movement away from the SC tissue 2916, a substrate change proximate to the lead 2918) at 2660.

For example, if the controller 251 detects the lead 402 has moved away from the SC tissue and/or stimulation target, the controller 251 may increase the amplitude of the pulses 2704-2712 forming the stimulation waveform 2702, increase the duration of pulses 2704-2712 of the stimulation waveform 2702, increase the number of pulses 2704-2712 forming the stimulation waveform 2702, and/or the like.

In another example, if the controller 251 detects the lead 402 has moved towards the SC tissue, the controller 251 may decrease the amplitude of the pulses 2704-2712 forming the stimulation waveform 2702, decrease the duration of pulses 2704-2712 of the stimulation waveform 2702, decrease the number of pulses 2704-2712 forming the stimulation waveform 2702, and/or the like.

Optionally, the controller 251 may have the IPG 250 stop delivering the stimulation waveform 2702. For example, if the controller 251 detects SC tissue damage, the controller 251 may have the IPG 250 stop delivering pulses 2704-2712 forming the stimulation waveform 2702 to the electrodes 511.

Additionally, or alternatively, the controller 251 may transmit to an external device, such as the system 100, via the far-field and/or near field communication circuitry 255 when the controller 251 detects damage to the SC tissue, a substrate change, or movement of the lead, at 2662. For example, the controller 251 may transmit an alert signal to the system 100 when the substrate proximate to the lead 402 has changed and/or neural damage of the SC tissue is detected.

The controller 251, the CPU 102, and the CPU 152 may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally, or alternatively, the controller 251, the CPU 102, and the CPU 152 may represent circuit modules that may be implemented as hardware with associated instructions (for example, software stored in a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The controller 251, the CPU 102, and the CPU 152 may execute a set of instructions that are stored in one or more storage elements, in order to process data. The storage elements may also store data or other information as desired or needed. The storage element may be in the form of an information source or a physical memory element within the controller 251, the CPU 102, and the CPU 152. The set of instructions may include various commands that instruct the controller 251, the CPU 102, and the CPU 152 to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. A method for detecting spinal cord tissue damage, comprising: applying electrical pulses from at least one electrode of a lead, wherein the lead is positioned proximate to spinal cord (SC) tissue;
   obtaining impedance measurements;
   obtaining evoked compound action potential (ECAP) measurements generated in response to the electrical pulses;
   determining an ECAP difference based on the ECAP measurements;
   determining an impedance difference based on the impedance measurements;
   distinguishing between at least two of i) SC tissue damage, ii) movement of the lead and iii) substrate change, based on predetermined combinations of the ECAP difference and the impedance difference; and
   adjusting at least one stimulation parameter to change the electrical pulses based on the distinguishing operation.

2. The method of claim 1, wherein the distinguishing distinguishes between i) the SC tissue damage and ii) the movement of the lead, relative to the SC tissue, based on the predetermined combination of the ECAP difference and the impedance difference.

3. The method of claim 1, wherein the distinguishing distinguishes between i) the SC tissue damage and ii) the substrate change based on the predetermined combination of the ECAP difference and the impedance difference, wherein the substrate change represents a change in a composition of SC tissue proximate spinal fluid.

4. The method of claim 1, further comprising detecting a direction of the movement of the lead, relative to the SC tissue, based on the predetermined combination of the ECAP difference and the impedance difference.

5. The method of claim 1, further comprising detecting a direction of the movement of the lead, relative to the SC tissue, in accordance with at least one of the following:
   a) lead movement away from the SC tissue when a second ECAP measurement decreases relative to a first ECAP measurement and a second impedance measurement increases relative to a first impedance measurement;
   b) lead movement away from the SC tissue when the second ECAP measurement decreases relative to the first ECAP measurement and the first and second impedance measurements are the same;
   c) lead movement toward the SC tissue when the second ECAP measurement increases relative to the first ECAP measurement and the second impedance measurement decreases relative to the first impedance measurement; or
   d) lead movement toward the SC tissue when the second ECAP measurement increases relative to the first ECAP measurement and the first and second impedance measurements are the same.

6. The method of claim 1, further comprising determining that the SC tissue damage is due to overstimulation or pressure from the lead based on a decrease or increase, respectively, in the ECAP difference.

7. The method of claim 1, further comprises determining that the SC tissue damage is due to overstimulation based on no change in the impedance difference.

8. A system for detecting spinal cord (SC) tissue damage comprising:
   an implantable pulse generator (IPG) in communication with a lead configured to be positioned proximate to spinal cord (SC) tissue, the lead including at least one electrode configured to apply electrical pulses;
   sensing circuitry configured to sense evoked compound action potential (ECAP) signals generated in response to the electrical pulses;
   a memory device configured to store programmed instructions; and
   a processor that, when executing the programmed instructions, is configured to:
     obtain impedance measurements;
     obtain ECAP measurements from the ECAP signals;
     determine an ECAP difference based on the ECAP measurements;
     determine an impedance difference based on the impedance measurements; and
     distinguish between at least two of i) SC tissue damage, ii) movement of the lead and iii) substrate change, based on predetermined combinations of the ECAP difference and the impedance difference; and
     adjust at least one stimulation parameter to change the electrical pulses based on the distinguishing operation.

9. The system of claim 8, wherein the processor is further configured to distinguish between i) the SC tissue damage and ii) the movement of the lead, relative to the SC tissue, based on the predetermined combination of the ECAP difference and the impedance difference.

10. The system of claim 8, wherein the processor is further configured to distinguish between i) the SC tissue damage and ii) the substrate change based on the predetermined combination of the ECAP difference and the impedance difference, wherein the substrate change represents a change in a composition of SC tissue proximate the spinal fluid.

11. The system of claim 8, wherein the processor is further configured to detect a direction of the movement of the lead, relative to the SC tissue, based on the predetermined combination of the ECAP difference and the impedance difference.

12. The system of claim 8, wherein the processor is further configured to detect a direction of the movement of the lead, relative to the SC tissue, in accordance with at least one of the following:
   a) lead movement away from the SC tissue when a second ECAP measurement decreases relative to a first ECAP measurement and a second impedance measurement increases relative to a first impedance measurement;
   b) lead movement away from the SC tissue when the second ECAP measurement decreases relative to the first ECAP measurement and the first and second impedance measurements are the same;
   c) lead movement toward the SC tissue when the second ECAP measurement increases relative to the first ECAP measurement and the second impedance measurement decreases relative to the first impedance measurement; or
   d) lead movement toward the SC tissue when the second ECAP measurement increases relative to the first ECAP measurement and the first and second impedance measurements are the same.

13. The system of claim 8, wherein the processor is further configured to determine that the SC tissue damage is due to overstimulation or pressure from the lead based on a decrease or increase, respectively, in the ECAP difference.

14. The system of claim 8, wherein the processor is further configured to determine that the SC tissue damage is due to overstimulation based on no change in the impedance difference.

* * * * *